(12) United States Patent
Watanabe

(10) Patent No.: US 8,138,355 B2
(45) Date of Patent: Mar. 20, 2012

(54) HETEROACENE DERIVATIVE, TETRAHALOTERPHENYL DERIVATIVE, AND PROCESSES FOR PRODUCING THE SAME

(75) Inventor: Makoto Watanabe, Yokkaichi (JP)

(73) Assignee: Tosoh Corporation, Shunan-Shi (JP)

( * ) Notice: Subject to any disclaimer, the term of this patent is extended or adjusted under 35 U.S.C. 154(b) by 40 days.

(21) Appl. No.: 12/439,341

(22) PCT Filed: Aug. 28, 2007

(86) PCT No.: PCT/JP2007/066684
§ 371 (c)(1),
(2), (4) Date: Feb. 27, 2009

(87) PCT Pub. No.: WO2008/026602
PCT Pub. Date: Mar. 6, 2008

(65) Prior Publication Data
US 2009/0261300 A1 Oct. 22, 2009

(30) Foreign Application Priority Data
Aug. 28, 2006 (JP) .................................. 2006-231082

(51) Int. Cl.
C07D 333/50 (2006.01)
(52) U.S. Cl. ................. 549/41; 252/301.16; 252/301.32; 428/690; 257/40; 549/29; 549/200; 549/216
(58) Field of Classification Search ............. 252/301.16, 252/301.32; 428/690; 257/40; 549/29, 200, 549/216
See application file for complete search history.

(56) References Cited

U.S. PATENT DOCUMENTS
2004/0076853 A1 4/2004 Jarikov
2008/0220285 A1* 9/2008 Vestweber et al. ............ 428/690

FOREIGN PATENT DOCUMENTS
| JP | 48-36439 B1 | 11/1973 |
| JP | 2005-120379 A | 5/2005 |
| JP | 2005-154371 A | 6/2005 |
| JP | 2007-19294 A | 1/2007 |
| WO | 03-016599 A1 | 2/2003 |
| WO | WO2006122630 | * 11/2006 |
| WO | 2007-068618 A1 | 6/2007 |

OTHER PUBLICATIONS

J. Chem. Soc., Perkin Trans. 1, Ahmed et al. 1973, 1099-1103.*
Macromolecules, 32, Haryono et al., 1999, 3146-3149.*
Cui-Hua Wang, et al; "Linear $C_2$-symmetric polycyclic benzodithiophene: efficient, highly diversified approaches and the optical properties"; Tetrahedron Letters, Oct. 10, 2005; vol. 46, No. 47; pp. 8153-8157.
Abdel-Meguid Osman; "Reactions between chloro-p-benzoquinones and β-naphthol"; Journal of Organic Chemistry, 1957, vol. 22, pp. 342-344.
Henning Sirringhaus, et al.; "Dibenzothienobisbenzothiophene—a novel fused-ring oligomer with high field-effect mobility."; Journal of Materials Chemistry; 1999; vol. 9 No. 9; pp. 2095-2101.
Hagen Klauk, et al.; "High-mobility polymer gate delectric pentacene thin film transistors"; American Institute of Physics; Nov. 2002; vol. 92, No. 9; pp. 5259-5263.
Henning Sirringhaus, et al.; "Integrated Optoelectronic Devices Based on Conjugated Polymers"; Science Magazine, Jun. 1998; vol. 280; pp. 1741-1744.
Kai Xiao, et al.; "A Highly π-Stacked Organic Semiconductor for Field-Effect Transistors Based on Linearly Condensed Penthathienoacene" J. Am. Chem. Soc. 2005; vol. 127, No. 38; pp. 13281-13286.
M. Doguchi et al.: "Polychlorinated Terphenyls in the Human Fat" Bulletin of Environmental Contamination & Toxicology, vol. 11, No. 2 1974, pp. 157-158.
P. M. Lahti: "A Semiempirical Investigation of Interelectronic Exchange Coupling in Bisected Poly(1,4-phenylene) Polycation Model Systems" International Journal of Quantum Chemistry, vol. 44, 1992, pp. 785-794. Extended European search report dated Jul. 7, 2010, issued in counterpart European Application No. 07806161.1-1211.
European Office Action dated May 25, 2011 issued in corresponding Application No. 07 806 161.1-1211.

* cited by examiner

Primary Examiner — Mark Kopec
Assistant Examiner — Haidung Nguyen
(74) Attorney, Agent, or Firm — Sughrue Mion, PLLC

(57) ABSTRACT

There are provided a heteroacene derivative having an excellent oxidation resistance and capable of forming a semiconductor active phase by a coating process, and an oxidation-resistant organic semiconductor material using the same, as well as an organic thin film.
A heteroacene derivative represented by the formula (1) is obtained by tetrametalation of a tetrahaloterphenyl derivative with a metalation agent and subsequent treatment of the resulting compound with reaction agents:

[Chem 1]

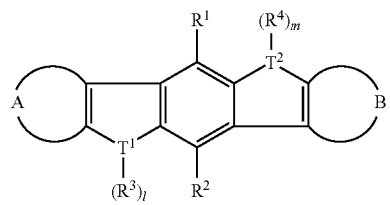

(1)

wherein the substituents $R^1$ to $R^4$ are the same or different and each represents a hydrogen atom, a fluorine atom, a chlorine atom, an aryl group having 4 to 30 carbon atoms, an alkyl group having 3 to 20 carbon atoms, or a halogenated alkyl group having 1 to 20 carbon atoms; $T^1$ and $T^2$ are the same or different and each represents sulfur, selenium, tellurium, oxygen, phosphorus, boron, or aluminum; l and m each is an integer of 0 or 1; and rings A and B are the same or different and each has a structure represented by the following formulae (A-1) or (A-2).

6 Claims, No Drawings

HETEROACENE DERIVATIVE, TETRAHALOTERPHENYL DERIVATIVE, AND PROCESSES FOR PRODUCING THE SAME

TECHNICAL FIELD

The present invention relates to a heteroacene derivative capable of development to electronic materials such as an organic semiconductor, a use thereof, and a process for producing the same. Furthermore, the invention relates to a tetrahaloterphenyl derivative which is a precursor compound of the heteroacene derivative, and a process for producing the same.

BACKGROUND ART

Recently, organic semiconductor devices represented by an organic thin-film transistor have attracted attention owing to characteristics such as saving of energy, low costs, and flexibility which inorganic semiconductor devices lack. The organic semiconductor device is composed of several kinds of materials such as an organic semiconductor active phase, a substrate, an insulating phase, and electrodes. Of these, an organic semiconductor active phase in charge of carrier movement of charges plays a primary role in the device. The performance of the organic semiconductor device is affected by the carrier mobility of an organic material constituting the organic semiconductor active phase.

As processes for preparing the organic semiconductor active phase, there are generally known a vacuum deposition process which is carried out by vaporizing an organic material at a high temperature under vacuum and a coating process wherein an organic material is dissolved in a suitable solvent and the solution is applied. In the coating process, the coating can be also carried out using a printing technology without using high-temperature and high-vacuum conditions. Accordingly, since a significant reduction of production costs of the device preparation can be achieved by printing, the coating process is a preferable process from an economical viewpoint. However, hitherto, there is a problem that it is increasingly difficult to form the organic semiconductor active phase from a material by the coating process as the performance of the material increases as an organic semiconductor device.

For example, it has been reported that a crystalline material such as pentacene has a high carrier mobility equal to amorphous silicon and exhibits the excellent organic semiconductor device properties (see, e.g., Non-Patent Document 1). Also, there has been reported an attempt to produce an organic semiconductor device by the coating process through dissolution of a polyacene such as pentacene (see Patent Document 1). However, since pentacene has a low solubility owing to its strong cohesiveness, high-temperature heating or the like conditions are necessary for applying the coating process. Furthermore, since a solution of pentacene is extremely easily oxidized with air, the application of the coating process involves difficulty from processing and economical viewpoints. Moreover, a self-assembling material such as poly(3-hexylthiophene) is soluble in a solvent and the preparation of an organic semiconductor device by coating has been reported. However, since the carrier mobility is one FIGURE lower than that of a crystalline compound (see, e.g., Non-Patent Document 2), there is a problem that the resulting organic semiconductor device shows a low performance.

Moreover, although pentathienoacene wherein thiophene rings are condensed exhibits an improved oxidation resistance as compared with pentacene, pentathienoacene is practically not a preferable material since carrier mobility is low and synthesis thereof requires many steps (see, e.g., Non-Patent Document 3).

Non-Patent Document 1: "Journal of Applied Physics", (USA), 2002, vol. 92, pp. 5259-5263
Non-Patent Document 2: "Science", (USA), 1998, vol. 280, pp. 1741-1744
Non-Patent Document 3: "Journal of American Chemical Society", (USA), 2005, vol. 127, pp. 13281-13286
Patent Document 1: WO2003/016599

DISCLOSURE OF THE INVENTION

Problems that the Invention is to Solve

Thus, in view of the problems of the above conventional technologies, an object of the invention is to provide a heteroacene derivative having excellent oxidation resistance and capable of forming an organic semiconductor active phase by a coating process and an oxidation-resistant organic semiconductor material using the same, as well as an organic thin film. Furthermore, another object of the invention is to provide a tetrahaloterphenyl derivative useful as a precursor for the heteroacene derivative and a process for producing the same.

Means for Solving the Problems

As a result of the extensive studies for solving the above problems, the present inventors have found a novel heteroacene derivative of the invention. In addition, since the heteroacene derivative is excellent in oxidation resistance and has the possibility of application of a coating process, so that a crystalline thin film can be easily and steadily prepared. Thus, they have found an oxidation-resistant organic semiconductor material comprising the heteroacene derivative and a thin film thereof and hence they have accomplished the invention.

Furthermore, the inventors have found a novel precursor compound, i.e., a specific tetrahaloterphenyl derivative capable of effectively producing the heteroacene derivative and have found a process for efficiently producing such a tetrahaloterphenyl derivative and hence they have accomplished the invention.

Namely, the invention includes the following composition.
1. A heteroacene derivative represented by the following formula (1):

[Chem 1]

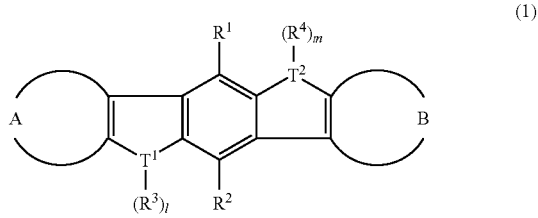

wherein the substituents $R^1$ to $R^4$ are the same or different and each represents a hydrogen atom, a fluorine atom, a chlorine atom, an aryl group having 4 to 30 carbon atoms, an alkyl group having 3 to 20 carbon atoms, or a halogenated alkyl group having 1 to 20 carbon atoms; $T^1$ and $T^2$ are the same or different and each represents sulfur, selenium, tellurium, oxygen, phosphorus, boron, or aluminum; l and m each represents an integer of 0 or 1; and rings A and B are the same or different and each has a structure represented by the following formulae (A-1) or (A-2):

[Chem 2]

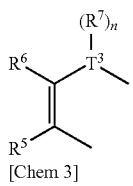

(A-1)

[Chem 3]

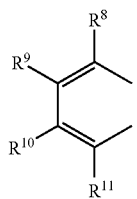

(A-2)

wherein the substituents $R^5$ to $R^{11}$ are the same or different and each represents a hydrogen atom, a fluorine atom, a chlorine atom, an aryl group having 4 to 30 carbon atoms, an alkyl group having 3 to 20 carbon atoms, or a halogenated alkyl group having 1 to 20 carbon atoms; any two or more respective substituents in each group of the substituents $R^5$ to $R^6$ and $R^8$ to $R^{11}$ may be together combined to form a benzene ring which may have a substituent, a pyridine ring which may have a substituent, or a pyrazine ring which may have a substituent; the substituent $T^3$ represents sulfur, Selenium, tellurium, oxygen, phosphorus, or boron; and n is an integer of 0 or 1; provided that the rings A and B each represents a ring represented by (A-1) or (A-2) having a substituent when $T^1$ and $T^2$ each is sulfur.

2. The heteroacene derivative according to the above 1, wherein l and m each is 0 and $T^1$ and $T^2$ are the same or different and each is sulfur, selenium, tellurium, or oxygen.

3. The heteroacene derivative according to the above 1, wherein l and m each is 1 and $T^1$ and $T^2$ are the same or different and each is phosphorus, boron, or aluminum.

4. The heteroacene derivative according to any one of the above 1 to 3, wherein n is 0 and $T^3$ is sulfur, selenium, tellurium, or oxygen.

5. A tetrahaloterphenyl derivative represented by the formula (2):

[Chem 4]

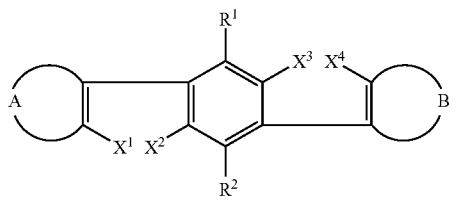

(2)

wherein the substituents $X^1$ to $X^4$ are the same or different and each represents a bromine atom, an iodine atom, a chlorine atom; and the substituents $R^1$, $R^2$ and the rings A, B represent the same meanings as those of the substituents and the rings represented in the formula (1) according to the above 1.

6. The tetrahaloterphenyl derivative according to the above 5, wherein the rings A and B each is a ring represented by (A-1) in the formula (2).

7. The tetrahaloterphenyl derivative according to the above 5 or 6, wherein n is 0 and $T^3$ is sulfur, selenium, tellurium, or oxygen.

8. A process for producing the heteroacene derivative according to any one of the above 1 to 4, which comprises tetrametalation of the tetrahaloterphenyl derivative represented by the formula (2) according to any one of the above 5 to 7 with a metalation agent and subsequent reaction of the resulting compound with reaction agents represented by the following formula (3) and the following formula (4):

$$(R^3)_l T^1 (L^1)_p \quad (3)$$

$$(R^4)_m T^2 (L^2)_q \quad (4)$$

wherein the substituents $T^1$, $T^2$, $R^3$, and $R^4$ and the symbols l and m represent the same meanings as those of the substituents and the symbols represented in the formula (1) according to the above 1 and the substituents $L^1$ and $L^2$ each represents a chlorine atom, a bromine atom, an iodine atom, an oxy group having 1 to 20 carbon atoms, an acetoxy groups or an arylsulfonyl group; and p and q each represents an integer of 0 or 2.

9. The process for producing the heteroacene derivative according to the above 8, wherein an alkyllithium is used as the metalation agent.

10. A process for producing the tetrahaloterphenyl derivative according to any one of the above 5 to 7, which comprises reacting a tetrahalobenzene represented by the following formula (5) with 2-haloarylmetal reagents represented by the following formula (6) and the following formula (7) in the presence of a palladium catalyst and/or a nickel catalyst:

[Chem 5]

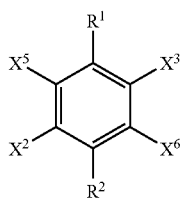

(5)

wherein the substituents $X^5$ and $X^6$ each represents a bromine atom, an iodine atom, or a chlorine atom; and the substituents $R^1$, $R^2$, $X^2$ and $X^3$ represent the same meanings as those of the substituents represented in the formula (2) according to the above 8;

[Chem 6]

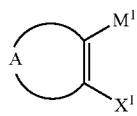

(6)

wherein $M^1$ represents a halide, a hydroxide, an alkoxide, or an alkylated product of magnesium, boron, zinc, tin, or silicone; the substituent $X^1$ and the ring A represent the same meanings as those of the substituent and the ring represented in the formula (2) according to the above 8;

[Chem 7]

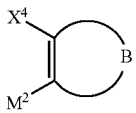
(7)

wherein $M^2$ represents a halide, a hydroxide, an alkoxide or an alkylated product of magnesium, boron, zinc, tin, or silicone; and the substituent $X^4$ and the ring B represent the same meanings as those of the substituent and the ring represented in the formula (2) according to the above 8.

11. The process for producing the tetrahaloterphenyl derivative according to the above 10, wherein, in the tetrahalobenzene represented by the formula (5), $X^5$ and $X^6$ each is an iodine atom and $X^2$ and $X^3$ each is a bromine atom and/or a chlorine atom.

12. The process for producing the tetrahaloterphenyl derivative according to the above 10 or 11, wherein $M^1$ and $M^2$ in the formula (6) and the formula (7) each is ZnCl or $B(OH)_2$.

13. The process for producing the tetrahaloterphenyl derivative according to any one of the above 10 to 12, wherein the catalyst to be used is tetrakis(triphenylphosphine)palladium.

14. An oxidation-resistant organic semiconductor material comprising the heteroacene derivative according to any one of the above 1 to 4.

15. An organic thin film, wherein the oxidation-resistant organic semiconductor material according to the above 14 is used.

16. The organic thin film according to the above 15, wherein the organic thin film is formed on a substrate.

Advantage of the Invention

There are provided a heteroacene derivative having an excellent oxidation resistance and capable of forming an organic semiconductor active phase by a coating process and a use thereof. Furthermore, there are also provided a tetrahaloterphenyl derivative which is a precursor compound of the heteroacene derivative, and a process for producing the same.

BEST MODE FOR CARRYING OUT THE INVENTION

The following will explain the present invention in detail. The explanation will be performed on a heteroacene derivative and the process for producing the same and a tetrahalotherphenyl derivative which is a precursor compound of the heteroacene derivative and a process for producing the same, as well as an oxidation-resistant organic semiconductor material comprising the heteroacene derivative and a thin film thereof.

(Heteroacene Derivative)

The heteroacene derivative of the invention is represented by the following formula (1):

[Chem 8]

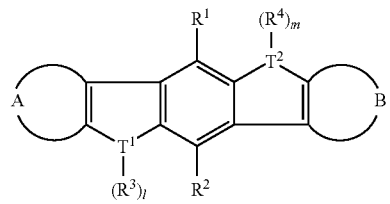
(1)

wherein the substituents $R^1$ to $R^4$ are the same or different and each represents a hydrogen atom, a fluorine atom, a chlorine atom, an aryl group having 4 to 30 carbon atoms, an alkyl group having 3 to 20 carbon atoms, or a halogenated alkyl group having 1 to 20 carbon atoms; $T^1$ and $T^2$ are the same or different and each represents sulfur, selenium, tellurium, oxygen, phosphorus, boron, or aluminum; l and m each is an integer of 0 or 1; and rings A and B are the same or different and each has a structure represented by the following formulae (A-1) or (A-2):

[Chem 9]

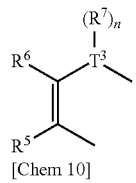
(A-1)

[Chem 10]

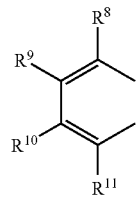
(A-2)

wherein the substituents $R^5$ to $R^{11}$ are the same or different and each represents a hydrogen atom, a fluorine atom, a chlorine atom, an aryl group having 4 to 30 carbon atoms, an alkyl group having 3 to 20 carbon atoms, or a halogenated alkyl group having 1 to 20 carbon atoms; any two or more respective substituents in each group of the substituents $R^5$ to $R^6$ and $R^8$ to $R^{11}$ may be together combined to form a benzene ring which may have a substituent, a pyridine ring which may have a substituent, or a pyrazine ring which may have a substituent; the substituent $T^3$ represents sulfur, selenium, tellurium, oxygen, phosphorus, or boron; and n is an integer of 0 or 1; provided that the rings A and B each represents a ring represented by (A-1) or (A-2) having a substituent when $T^1$ and $T^2$ each is sulfur.

The following will further describe the substituents of the heteroacene derivative of the formula (1) of the invention.

The aryl group having 4 to 30 carbon atoms in the substituents $R^1$ to $R^4$ is not particularly limited and examples thereof may include a phenyl group, a p-tolyl group, a p-(n-hexyl) phenyl group, a p-(n-octyl)phenyl group, a p-(cyclohexyl)

phenyl group, a m-(n-octyl)phenyl group, a p-fluorophenyl group, a pentafluorophenyl group, a p-(trifluoromethyl)phenyl group, a p-(n-perfluorooctyl)phenyl group, a 2-thienyl group, a 5-(n-hexyl)-2-thienyl group, a 2,2'-bithienyl-5-group, a biphenyl group, a perfluorobiphenyl group, a 1-naphthyl group, a 2-naphthyl group, a 1-perfluoronaphthyl group, an anthracenyl group, a 2-fluorenyl group, a 9,9-dimethyl-2-fluorenyl group, a 1-biphenyleno group, a 2-biphenyleno group, a terphenyl group, a 2-pyridyl group, a tetrafluoropyridyl group, a bipyridyl group, a (diphenylamino) phenyl group, a (diphenylamino)biphenyl group, and the like, and is preferably a phenyl group, a p-(n-octyl)phenyl group, a p-(n-perfluorooctyl)phenyl group, a 5-(n-hexyl)-2-thienyl group, and the like.

The alkyl group having 3 to 20 carbon atoms in the substituents $R^1$ to $R^4$ is not particularly limited and examples thereof may include a propyl group, an n-butyl group, an isobutyl group, a t-butyl group, a neopentyl group, a hexyl group, an octyl group, a dodecyl group, an octadecyl group, a cyclohexyl group, a cyclooctyl group, an 2-ethylhexyl group, and the like.

The halogenated alkyl group having 1 to 20 carbon atoms in the substituents $R^1$ to $R^4$ is not particularly limited and examples thereof may include perfluoroalkyl groups such as a trifluoromethyl group, a trifluoroethyl group, a perfluorooctyl group, a perfluorododecyl group, a perfluorooctadecyl group, a perfluorocyclohexyl group, and a perfluorocyclooctyl group; or halogenated alkyl groups wherein part of hydrogen is replaced with fluorine, such as a pentadecafluorooctyl group and an octadecafluorodecyl group, and preferred are perfluoroalkyl groups and particularly preferred are a perfluorooctyl group and a perfluorododecyl group.

Among these substituents $R^1$ to $R^4$, particularly, a hydrogen atom and an aryl group having 4 to 30 carbon atom are preferred and further, a hydrogen atom and a phenyl group are preferred.

The substituents $T^1$ and $T^2$ each is sulfur, selenium, tellurium, oxygen, phosphorus, boron, or aluminum, preferably sulfur, selenium, phosphorus, or boron, and further preferably sulfur, phosphorus, or boron. Moreover, when $T^1$ and $T^2$ each is sulfur, the rings A and B each is preferably a ring represented by (A-1) or (A-2) having a substituent.

l and m each is an integer of 0 or 1. However, when the substituents $T^1$ and $T^2$ each is sulfur, selenium, tellurium, or oxygen, l and m each is 0 and when the substituents $T^1$ and $T^2$ each is phosphorus, boron, or aluminum, l and m each is 1.

The following will describe the rings A and B represented by the formulae (A-1) and (A-2).

The heteroacene derivative of the invention is a derivative having the rings A and B and the rings A and B each has a structure represented by the formulae (A-1) or (A-2).

The aryl group having 4 to 30 carbon atoms in the substituents $R^5$ to $R^{11}$ is not particularly limited and examples thereof may include a phenyl group, a p-tolyl group, a p-(n-hexyl) phenyl group, a p-(n-octyl)phenyl group, a p-(cyclohexyl) phenyl group, a m-(n-octyl)phenyl group, a p-fluorophenyl group, a pentafluorophenyl group, a p-(trifluoromethyl)phenyl group, a p-(n perfluorooctyl)phenyl group, a 2-thienyl group, a 5-(n-hexyl)-2-thienyl group, a 2,2'-bithienyl-5-group, a biphenyl group, a perfluorobiphenyl group, a 1-naphthyl group, a 2-naphthyl group, a 1-perfluoronaphthyl group, an anthracenyl group, a 2-fluorenyl group, a 9,9-dimethyl-2-fluorenyl group, a 1-biphenyleno group, a 2-biphenyleno group, a terphenyl group, a 2-pyridyl group, a tetrafluoropyridyl group, a bipyridyl group, a (diphenylamino) phenyl group, a (diphenylamino)biphenyl group, and the like, and preferred are a phenyl group, a p-(n-octyl)phenyl group, a p-(n-perfluorooctyl)phenyl group, a 5-(n-hexyl)-2-thienyl group, and the like.

The alkyl group having 3 to 20 carbon atoms in the substituents $R^5$ to $R^{11}$ is not particularly limited and examples thereof may include a propyl group, an n-butyl group, an isobutyl group, a t-butyl group, a neopentyl group, a hexyl group, an octyl group, a dodecyl group, a cyclohexyl group, a cyclooctyl group, an 2-ethylhexyl group, and the like.

The halogenated alkyl group having 1 to 20 carbon atoms in the substituents $R^5$ to $R^{11}$ is not particularly limited and examples thereof may include a trifluoromethyl group, a trifluoroethyl group, a perfluorooctyl group, a perfluorocyclohexyl group, and a perfluorocyclooctyl group, and the like, and preferred is a perfluorooctyl group.

Moreover, any two or more respective substituents in each group of the substituents $R^5$ to $R^6$ and $R^8$ to $R^{11}$ of the rings A and B may be together combined to form a benzene ring which may have a substituent, a pyridine ring which may have a substituent, or a pyrazine ring which may have a substituent, and preferred is a benzene ring which may have a substituent. The benzene ring which may have a substituent is not particularly limited and examples thereof may include a benzene ring, a methylbenzene ring, an (n-hexyl)benzene ring, an (n-octyl)benzene ring, a dimethylbenzene ring, a di(n-hexyl) benzene ring, a diphenylbenzene ring, a naphthalene ring, a methylnaphthalene ring, a dimethylnaphthalene ring, a di(n-hexyl)naphthalene ring, a di(n-octyl)naphthalene ring, a di(n-dodecyl)naphthalene ring, a di(n-octadecyl)naphthalene ring, a di(2-ethylhexyl)naphthalene ring, a di(n-perfluorohexyl)naphthalene ring, a di(n-perfluorooctyl)naphthalene ring, a di(n-perfluorododecyl)naphthalene ring, a di(n-perfluorooctadecyl)naphthalene ring, a di(n-pentadecafluorooctyl)naphthalene ring, a di(n-octadecafluorododecyl)naphthalene ring, a phenylnaphthalene ring, an anthracene ring, a triphenylene ring, a quinoline ring, and the like. The pyridine ring which may have a substituent is not particularly limited and examples thereof may include a pyridine ring, a methylpyridine ring, an (n-hexyl)pyridine ring, a phenylpyridine ring, and the like. The pyrazine ring which may have a substituent is not particularly limited and examples thereof may include a pyrazine ring, a methylpyrazine ring, a dimethylpyrazine ring, an (n-hexyl)pyrazine ring, a phenylpyrazine ring, and the like. A benzene ring which may have a substituent is preferred and further, a di(n dodecyl)naphthalene ring and a di(n-perfluorododecyl)naphthalene ring are particularly preferred. Moreover, among the substituents $R^8$ to $R^{11}$, $R^9$ and $R^{10}$ are preferably together combined to form a benzene ring which may have a substituent.

Among these substituents $R^5$ to $R^6$ and $R^8$ and $R^{11}$, a hydrogen atom, a fluorine atom, and a benzene ring which may have a substituent are preferred and further, a hydrogen atom, a fluorine atom, and a benzene ring are preferred.

The substituent $T^3$ is sulfur, selenium, tellurium, oxygen, phosphorus, or boron, preferably sulfur, selenium, phosphorus, or boron, and further preferably sulfur, phosphorus, or boron.

n is an integer of 0 or 1. When n is 0, $T^3$ is sulfur, selenium, tellurium, or oxygen and when n is 1, $T^3$ is phosphorus or boron.

Among them, as the heteroacene derivatives represented by the formula (1) of the invention, preferred are the following compounds since the heteroacene derivatives, oxidation-resistant organic semiconductor materials containing the heteroacene derivatives, and organic thin films thereof exhibit high oxidation resistance and carrier mobility:

[Chem 11]
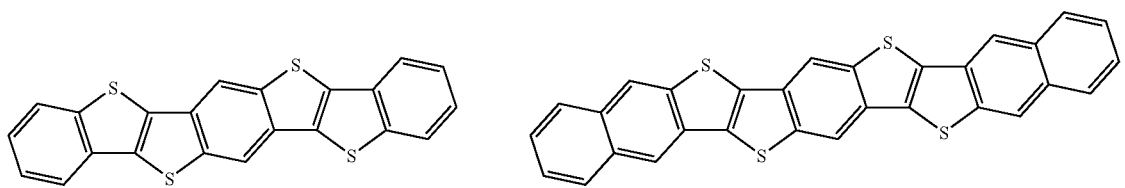
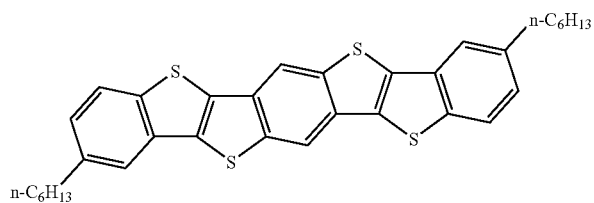
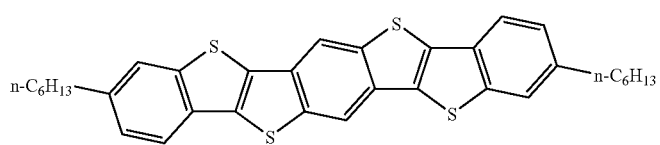
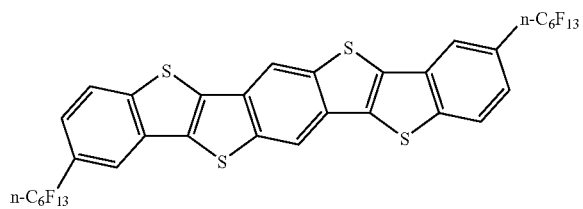
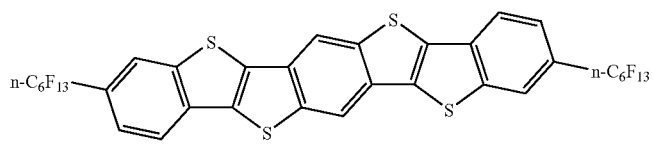
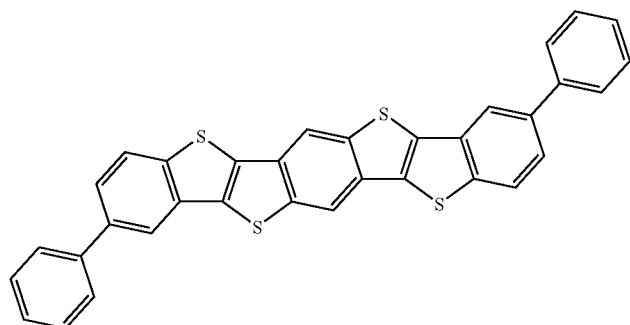
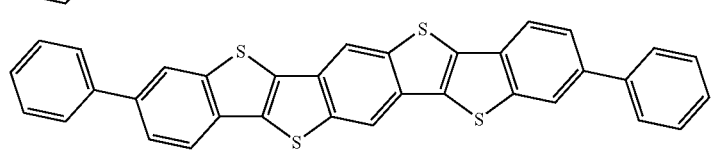

-continued
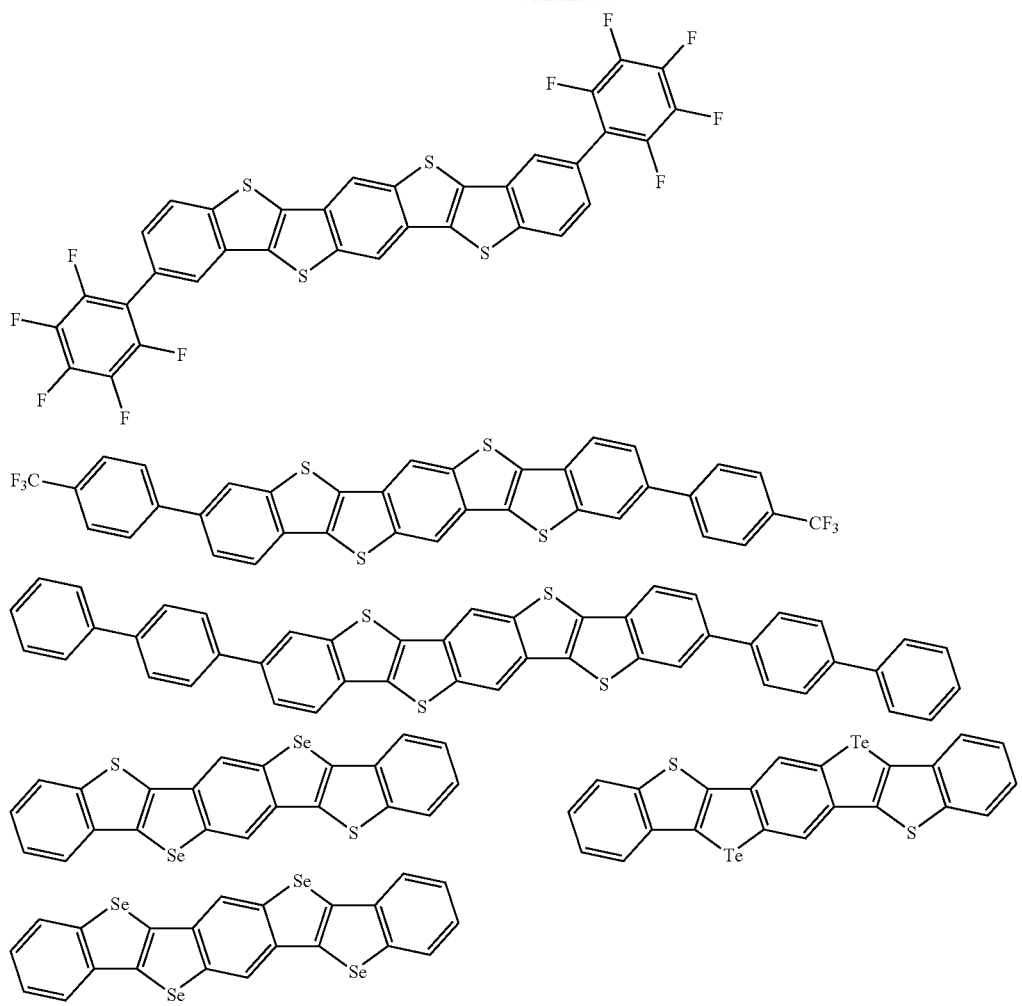
[Chem 12]
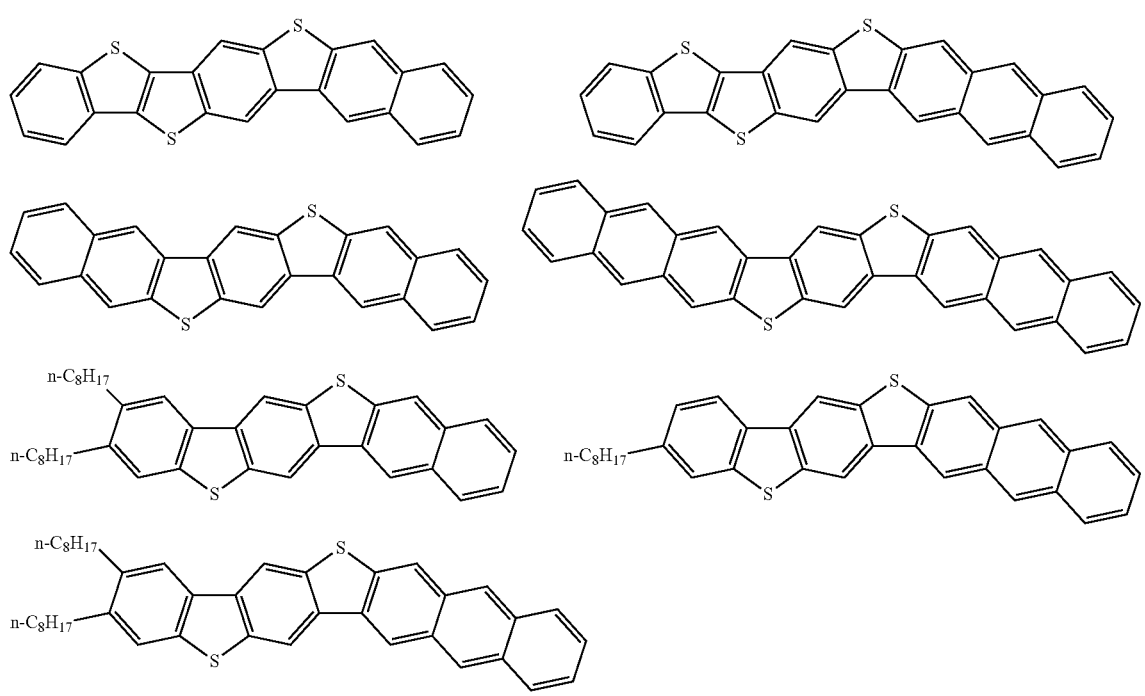

-continued
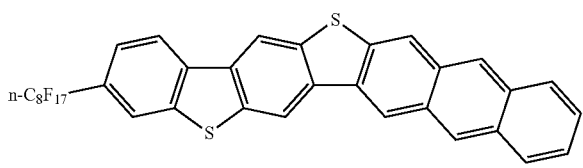
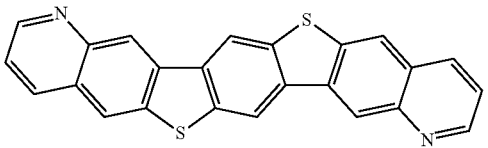
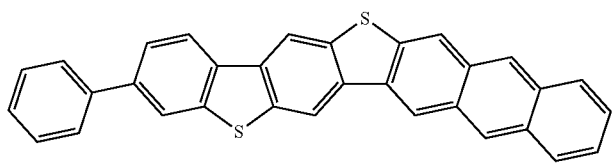
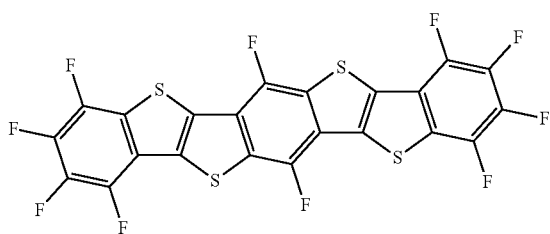
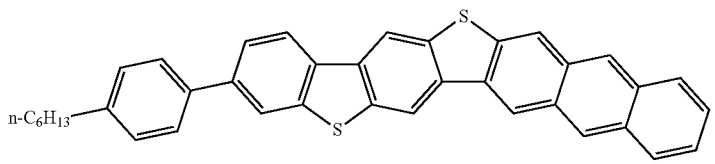
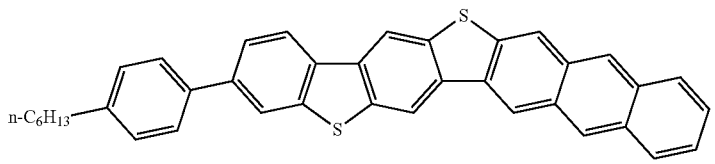
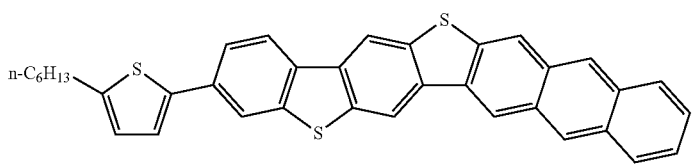
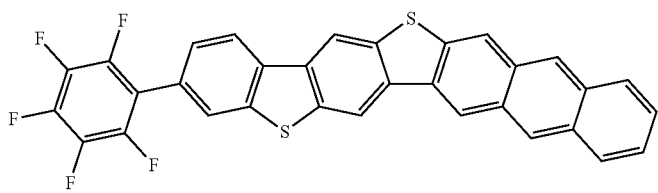
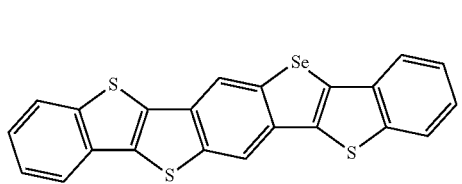
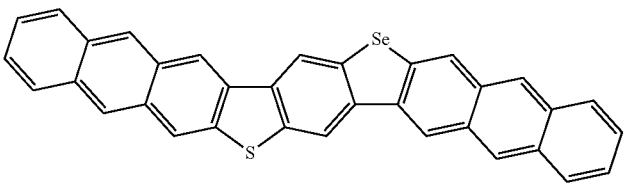
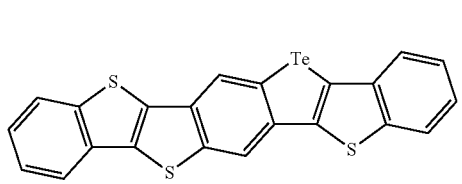
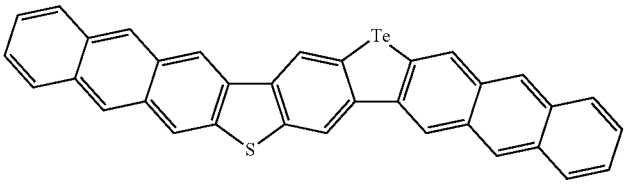

-continued
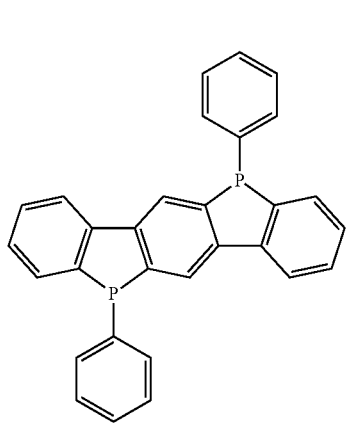 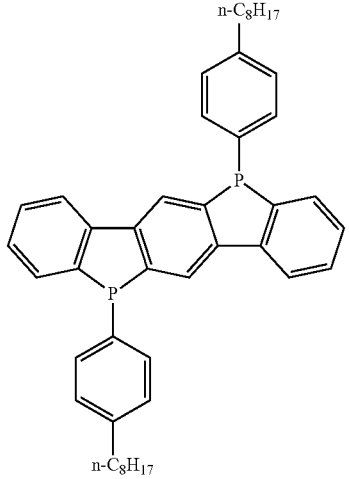 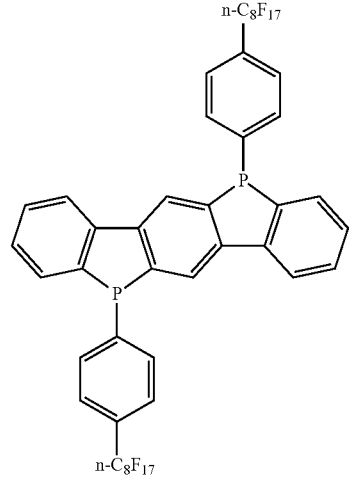
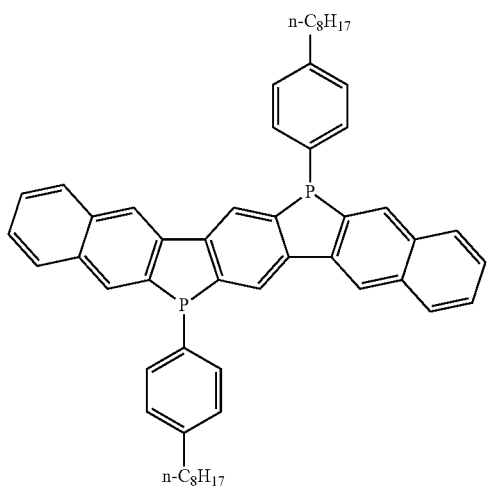 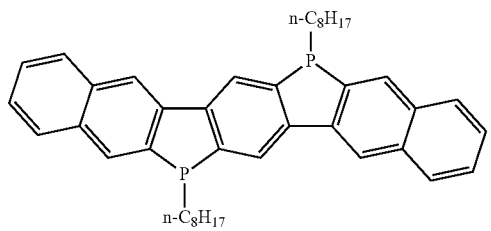
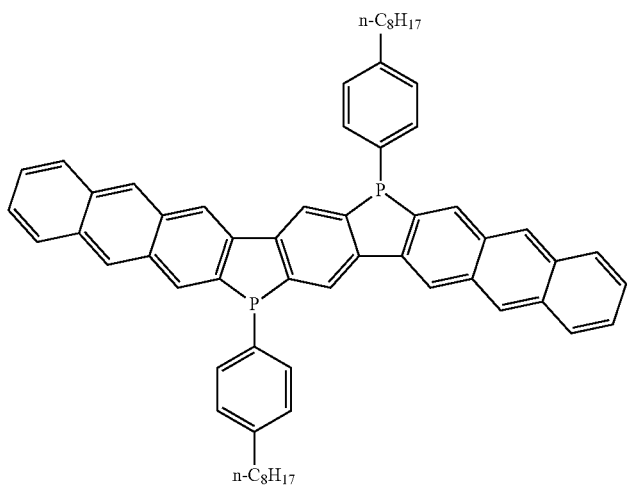 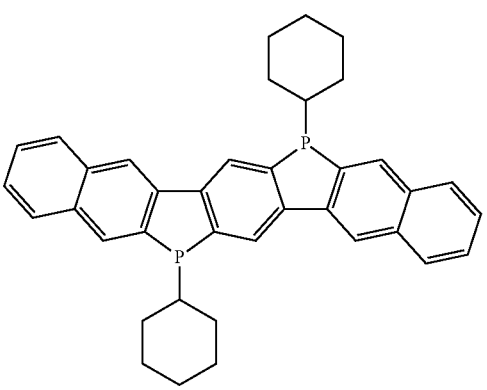

-continued
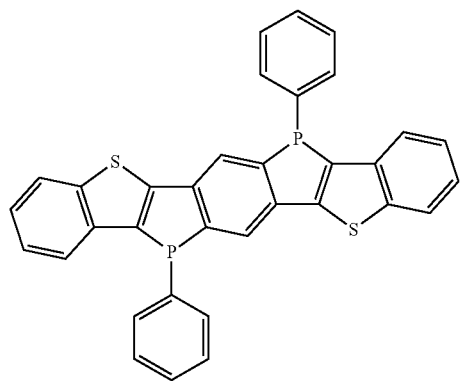
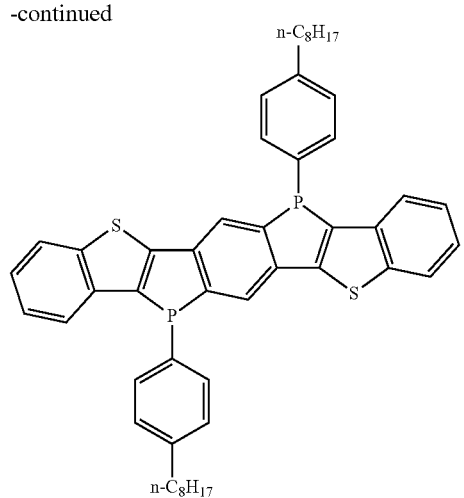
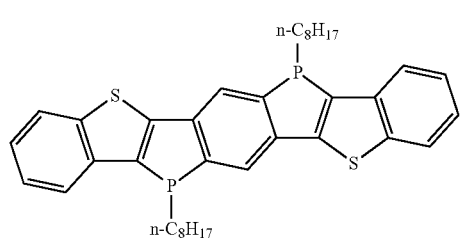
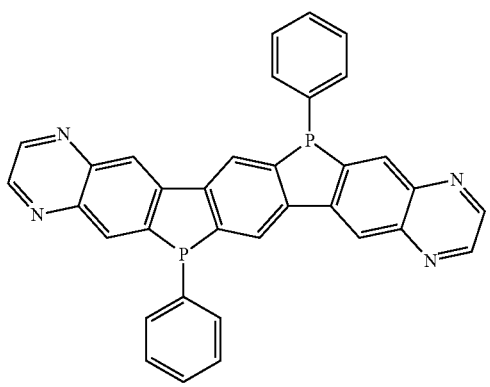
[Chem 14]
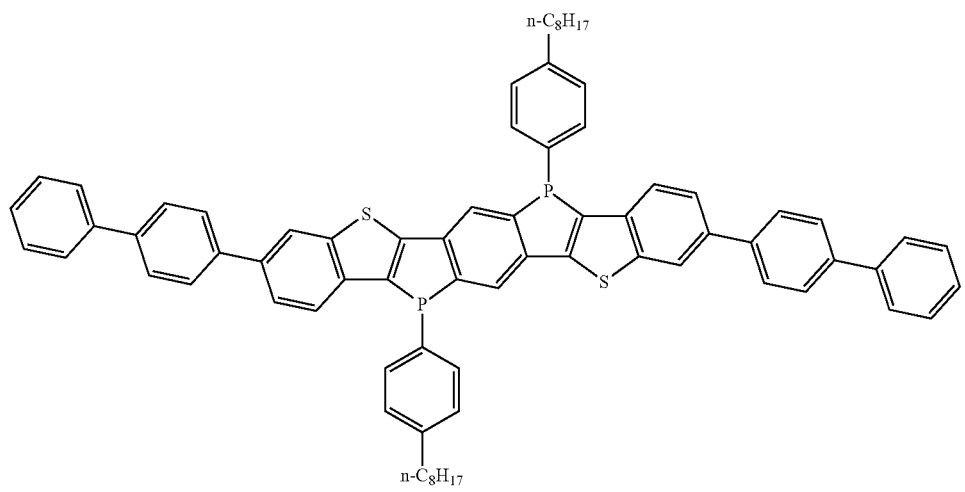

19
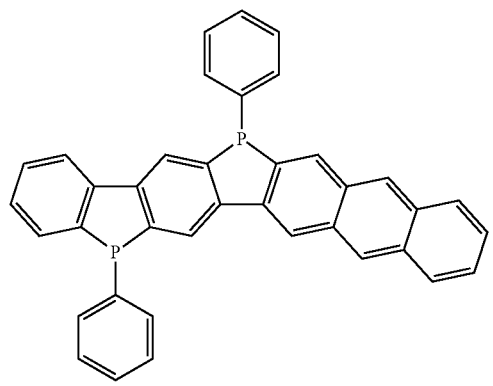
20
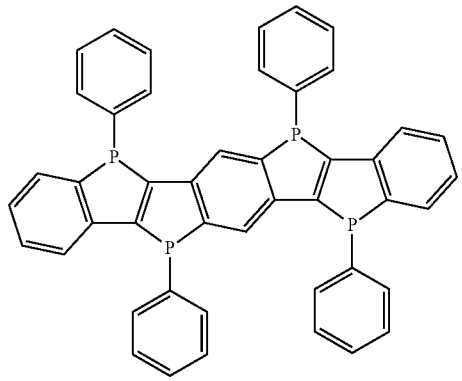
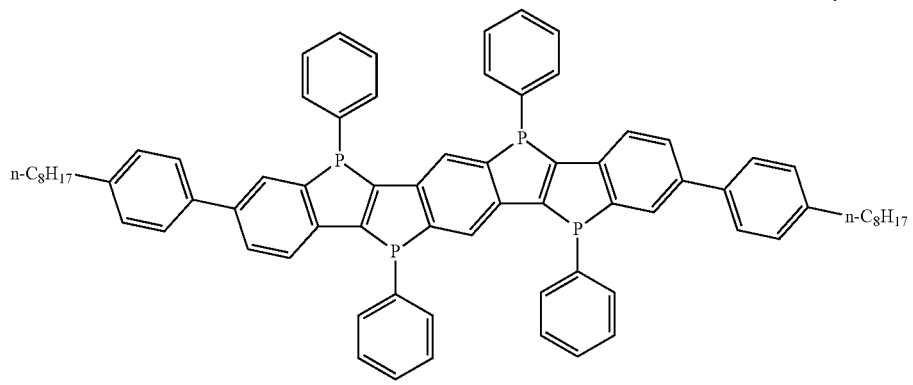
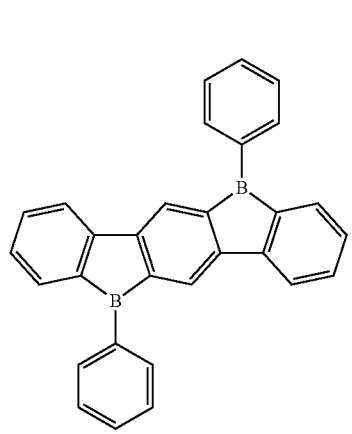
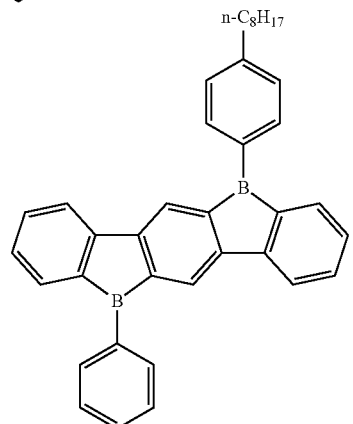
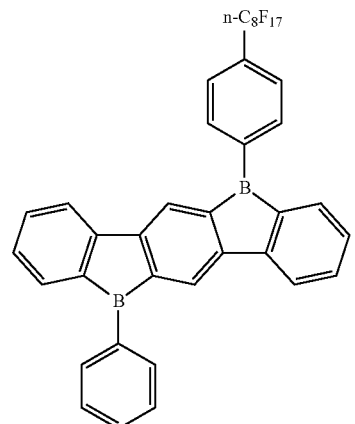
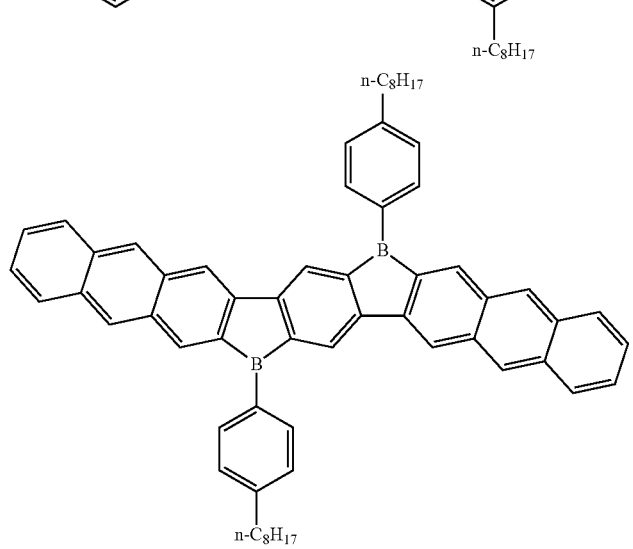
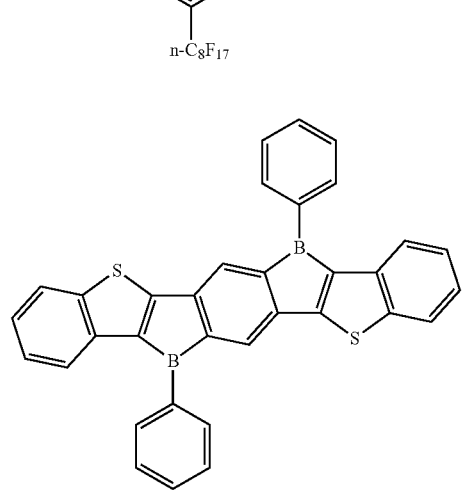

-continued
21
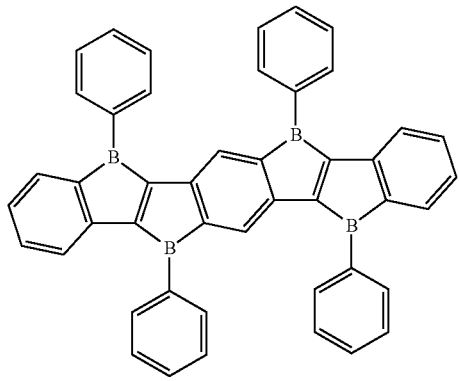
22
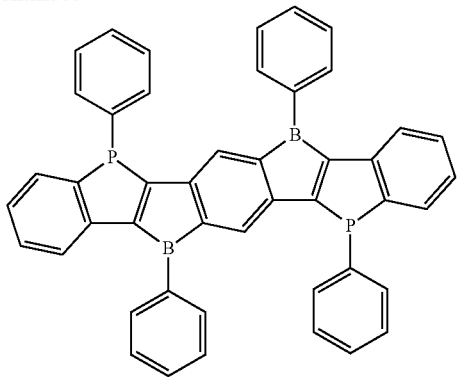
[Chem 15]
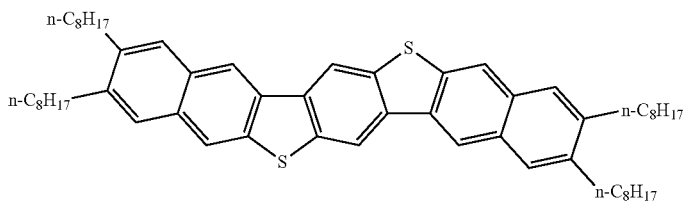
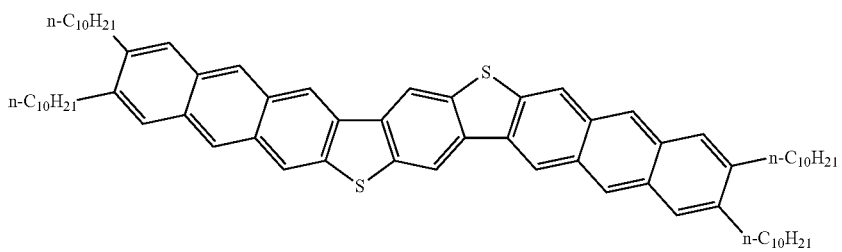
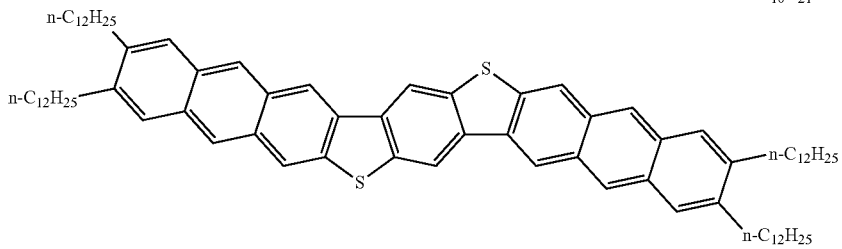
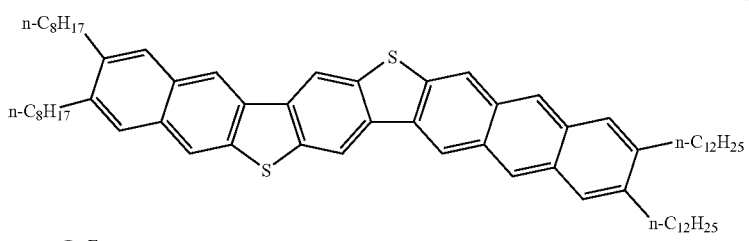
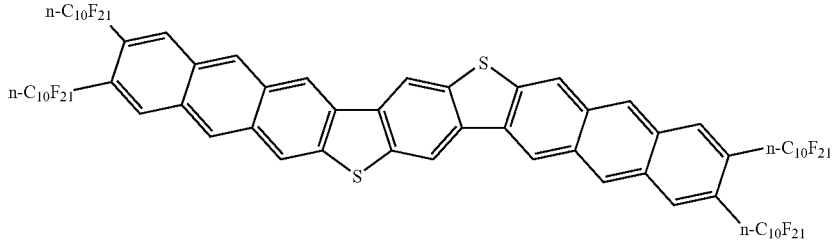

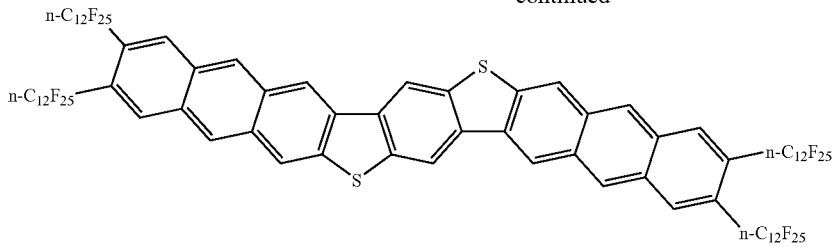

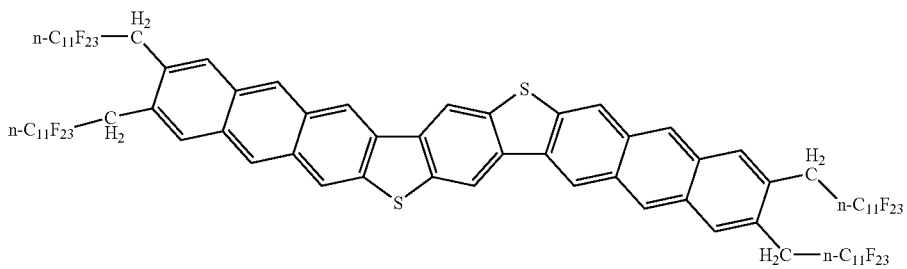

Particularly, tetrathienoacene, P,P-diphenylbenzophospholodibenzophosphole, B,B-diphenylbenzoborolyldibenzoborole, tetrafluorodithienoacene, tetraphenyldithienoacene, dibenzodithienoacene, and the like are preferred.

(Tetrahaloterphenyl Derivative)

The following will describe the tetrahaloterphenyl derivative which is a precursor compound of the heteroacene derivative represented by the formula (1) of the invention.

The tetrahaloterphenyl derivative which is a precursor compound of the heteroacene derivative represented by the formula (1) of the invention is represented by the following formula (2):

[Chem 16]

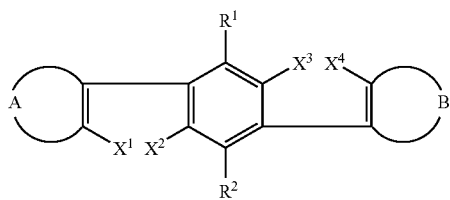

(2)

wherein the substituents $X^1$ to $X^4$ each represents a bromine atom, an iodine atom, or a chlorine atom; and the substituents $R^1$, $R^2$ and the rings A, B represent the same meanings as those of the substituents and the rings represented in the formula (1).

The substituents $X^1$ to $X^4$ each represents a bromine atom, an iodine atom, or a chlorine atom, and is preferably a bromine atom or an iodine atom and particularly preferably a bromine atom.

The substituents $R^1$ and $R^2$ represent the same meanings as those of the substituents represented in the formula (1) and, among them, particularly, a hydrogen atom is preferred.

The rings A and B represent the same meanings as those of the rings represented in the formula (1). Namely, they represent the same meanings as the formula (A-1) or the formula (A-2). Among them, in the formula (A-1), it is preferred that $T^3$ is sulfur and $R^5$ and $R^6$ are combined to form a cyclic benzene ring. Also, in the formula (A-2), $R^8$ to $R^{11}$ each is preferably a hydrogen atom, a fluorine atom, or a cyclic benzene ring.

As the tetrahaloterphenyl derivative represented by the formula (2) of the invention, the following compounds are preferred:

[Chem 17]

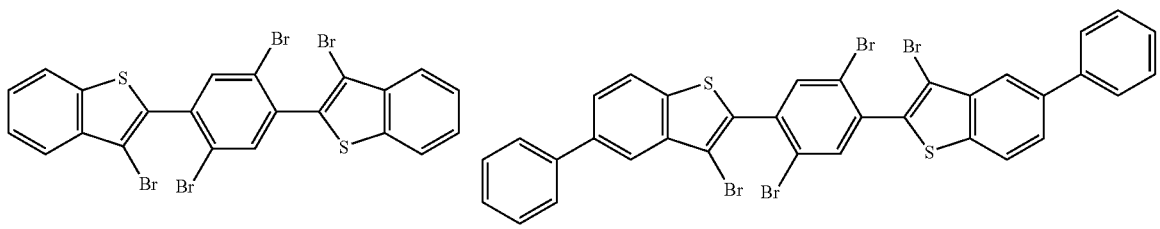

-continued
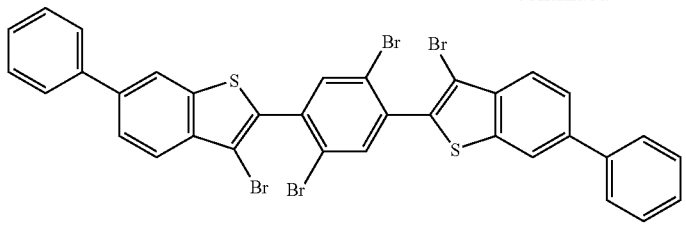
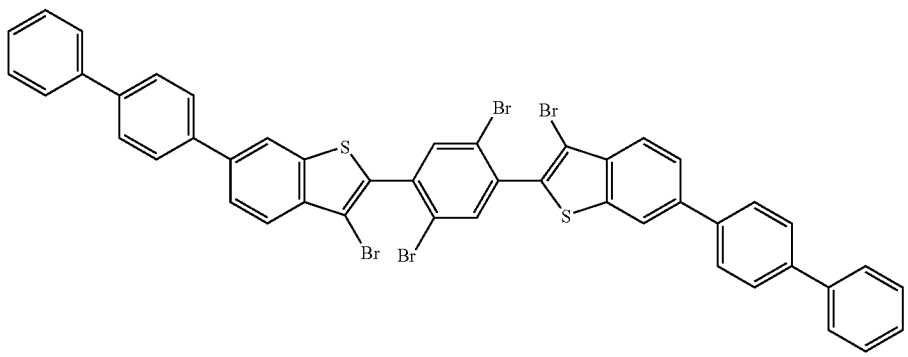
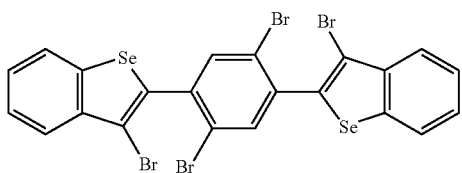
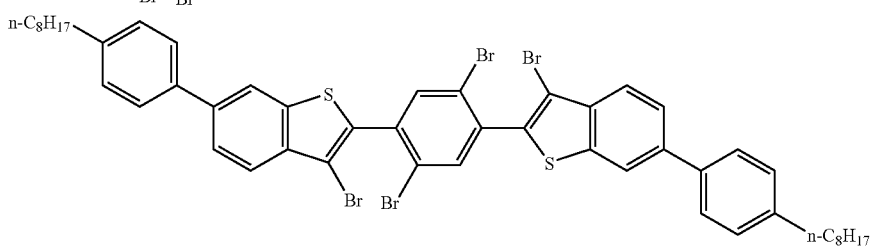
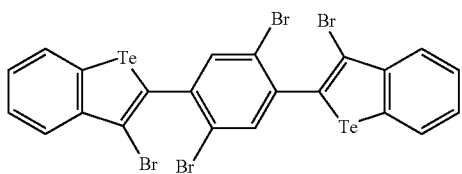
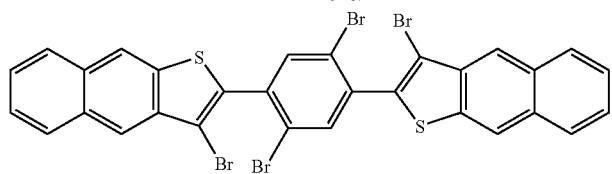
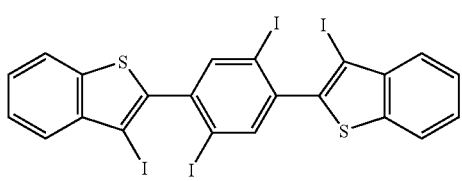
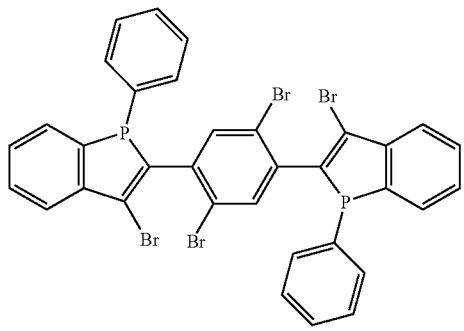

-continued
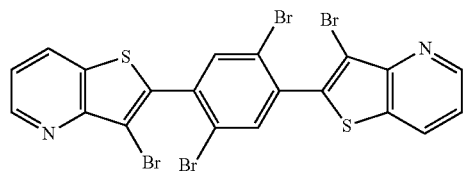
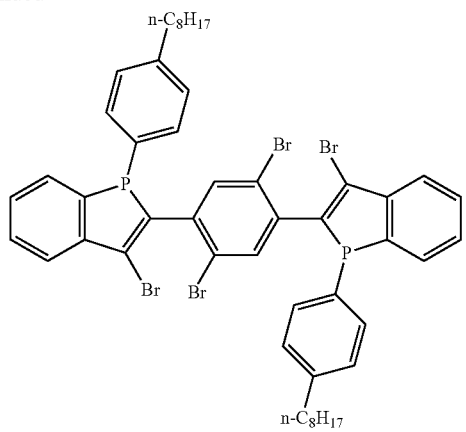
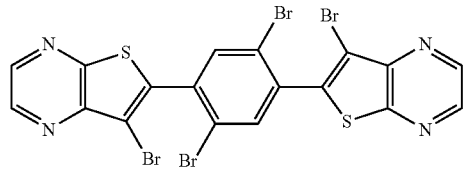
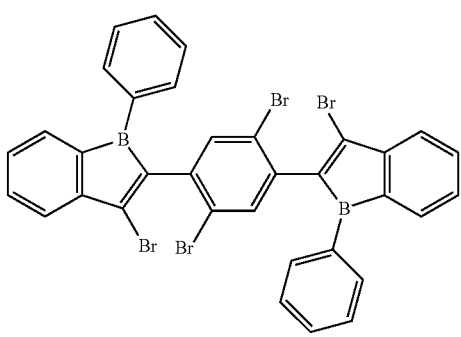
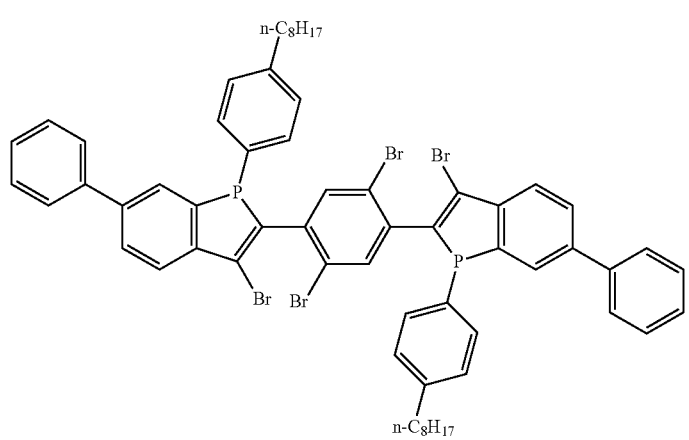
[Chem 18]
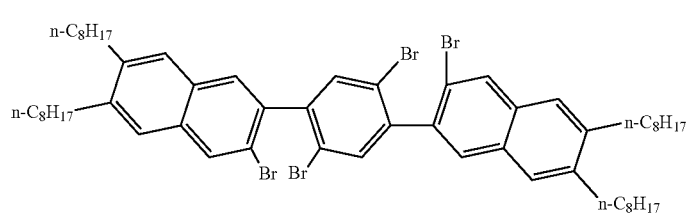
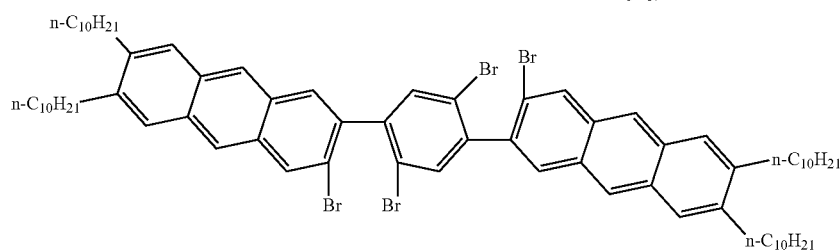

-continued
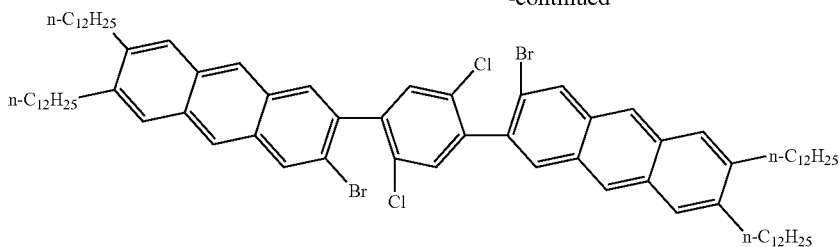
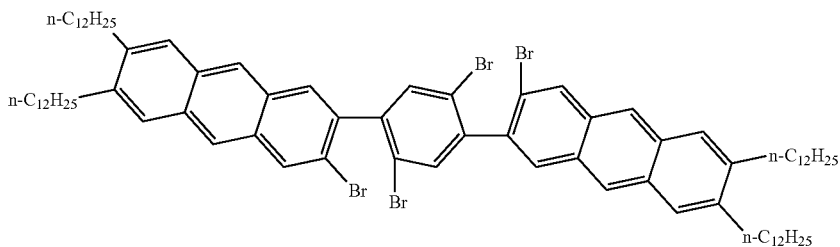
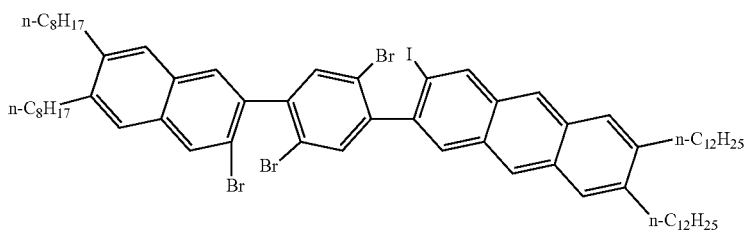
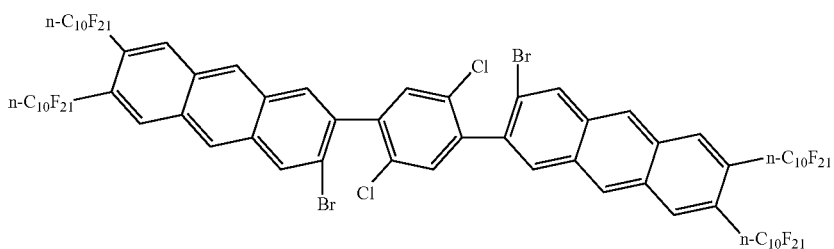
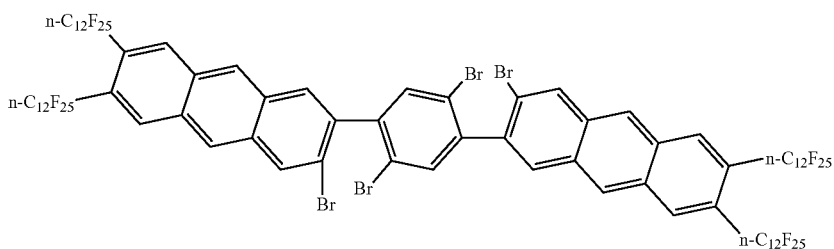
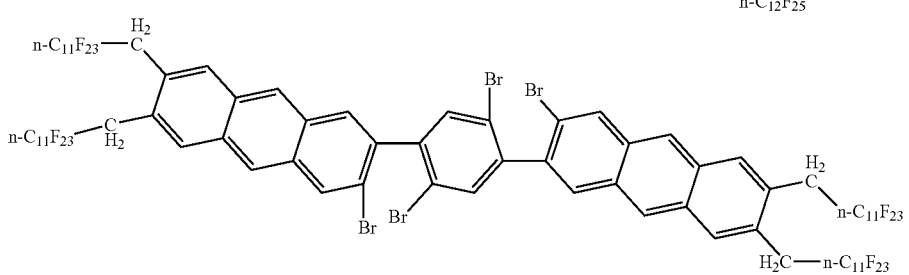

In particular, {1,4-bis(3-bromobenzothienyl)-2,5-dibromo}benzene, 2,2',5',2''-tetrabromo-1,1',4',1''-terphenyl, 4,5,4'',5''-tetrafluoro-2,2',5',2''-tetrabromo-1,1',4',1''-terphenyl, 4,5,4'',5''-tetraphenyl-2,2',5',2''-tetrabromo-1,1',4',1''-terphenyl, and 2,2',5',2''-tetrabromo-1,1',4',1''-dibenzoterphenyl are preferred.

(Process for Producing Heteroacene Derivative)

The following will describe the process for producing the heteroacene derivative represented by the formula (1) of the invention.

The heteroacene derivative represented by the formula (1) of the invention can be produced by tetrametalation of the tetrahaloterphenyl derivative represented by the formula (2) with a metalation agent and subsequent reaction of the resulting compound with reaction agents represented by the following formula (3) and the following formula (4). In this connection, the reaction agents represented by the formula (3) and the formula (4) may be the same.

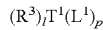  (3)

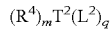  (4)

wherein the substituents $T^1$, $T^2$, $R^3$, $R^4$ and the symbols l and m represent the same meanings as those of the substituents and the symbols represented in the formula (1) and the substituents $L^1$ and $L^2$ each represents a chlorine atom, a bromine atom, an iodine atom, an oxy group having 1 to 20 carbon atoms, an acetoxy group, or a phenylsulfonyl group; and p and q each represents an integer of 0 or 2.

In this connection, the tetrametalation means replacement of each of $X^1$ to $X^4$ in the formula (2) with a metal.

In the case where the tetrahaloterphenyl derivative represented by the formula (2) is subjected to tetrametalation, the metalation agent to be used is not particularly limited so far as it can replace each of $X^1$ to $X^4$ in the formula (2) with a metal and examples thereof may include alkyllithiums such as n-butyllithium, sec-butyllithium, tert-butyllithium, methyllithium, and hexyllithium; aryllithiums such as phenyllithium, p-tert-butylphenyllithium, p-methoxyphenyllithium, and p-fluorophenyllithium; lithium amides such as lithium diisopropylamide and lithium hexamethyldisilazide; and lithium metal such as lithium powder; Grignard reagents such as methylmagnesium bromide, ethylmagnesium bromide, isopropylmagnesium chloride, tert-butylmagnesium chloride, and phenylmagnesium bromide; magnesium metal; zinc metal; and the like. Preferred is an alkyllithium and particularly preferred is sec-butyllithium.

The amount of the metalation agent to be used is in the range of preferably 3 to 20 equivalents, particularly preferably 4 to 15 equivalents, further preferably 5 to 10 equivalents to the tetrahaloterphenyl derivative represented by the formula (2).

The tetrametalation is preferably carried out in a solvent. The solvent to be used is not particularly limited and examples thereof are tetrahydrofuran (hereinafter abbreviated as THF), diethyl ether, methyl tert-butyl ether, ethylene glycol dimethyl ether, dioxane, toluene, hexane, cyclohexane, and the like. Particularly preferred is THF. Also, these solvents may be used singly or as a mixture of two or more thereof. The temperature for the tetrametalation is preferably from –100 to 50° C., particularly preferably from –90 to 20° C. The reaction time is preferably from 1 to 120 minutes, particularly preferably from 5 to 60 minutes. In this connection, the progress of the tetrametalation can be monitored by taking out a portion of the reaction liquid and, after stopping the reaction with water, analyzing it by gas chromatography.

The tetrametal salt formed by the tetrametalation reaction is subsequently reacted with the reaction agents represented by the formula (3) and the formula (4) to obtain the heteroacene derivative represented by the formula (1). For such a reaction with the reaction agents, either of a method of reacting the reaction mixture containing the tetrametal salt formed by the above tetrametalation with direct use of the above reaction agents or a method of once isolating the formed tetrametal salt and then reacting it with the above reaction agents may be used.

The substituents $T^1$, $T^2$, $R^3$ and $R^4$ and the symbols l and m in the formula (3) and the formula (4) represent the same meanings as those of the substituents and the symbols represented in the formula (1). Among them, as the formula (3) and the formula (4), bis(phenylsulfonyl)sulfide, dichlorophenylphosphine, dichlorophenylborane, and the like are preferred.

Moreover, the substituents $L^1$ and $L^2$ each represents a chlorine atom, a bromine atom, an iodine atom, an oxy group having 1 to 20 carbon atoms, an acetoxy group, or an arylsulfonyl group, and preferred is a chlorine atom, a bromine atom, an oxy group having 1 to 20 carbon atoms, or an arylsulfonyl group. The oxy group having 1 to 20 carbon atoms is not particularly limited and examples thereof may include a methoxy group, an ethoxy group, an n-butoxy group, a phenoxy group, a (2-methoxy)phenoxy group, and the like. The arylsulfonyl group is not particularly limited and examples thereof may include a phenylsulfonyl group, a p-tolylsulfonyl group, and the like. Among them, particularly, a phenylsulfonyl group is preferred.

Specific examples of the reaction agents represented by the formula (3) and the formula (4) may include sulfur dichloride; sulfur dibromide; bis(arylsulfonyl)sulfides such as bis(phenylsulfonyl)sulfide and bis(p-tolylsulfonyl)sulfide; sulfur; selenium dichloride; selenium; tellurium dichloride; tellurium; arylphosphines such as dichlorophenylphosphine, dimethoxyphenylphosphine, diphenoxyphenylphosphine, and dichloro{4-(n-octyl)phenyl}phosphine; alkylphosphines such as dichloro(n-hexyl)phosphine, dichloro(n-octyl)phosphine, and dimethoxy(n-hexyl)phosphine; arylboranes such as dichlorophenylborane, dimethoxyphenylborane, dimethoxy{4-(n-hexyl)phenyl}borane, diphenoxyphenylborane, and dichloro{4-(n-octyl)phenyl}borane; alkylboranes such as dichloro(n-hexyl)borane, dichloro(n-octyl)borane, and dimethoxy(n-hexyl)borane; arylaluminums such as dichlorophenylaluminum, dimethoxyphenylaluminum, dimethoxy{4-(n-hexyl)phenyl}aluminum, diphenoxyphenylaluminum, and dichloro{4-(n-octyl)phenyl}aluminum; alkylaluminums such as dichloro(n-hexyl)aluminum, dichloro(n-octyl)aluminum, and dimethoxy(n-hexyl)aluminum; and the like. Preferred are bis(phenylsulfonyl)sulfide, dichlorophenylphosphine, dichlorophenylborane, and the like.

The reaction of the tetrametal salt formed by tetrametalation with the reaction agents represented by the formula (3) and the formula (4) is preferably carried out in a solvent. The solvent to be used is not particularly limited and examples thereof are THF, diethyl ether, methyl tert-butyl ether, ethylene glycol dimethyl ether, diglyme, dioxane, toluene, hexane, cyclohexane, and the like. Particularly preferred is THF. Also, the amount of the reaction agents to be used is preferably from 1.2 to 10 equivalents, and particularly preferably 2 to 8 equivalents to the tetrahaloterphenyl derivative represented by the formula (2). The temperature for the reaction with the reaction agents is preferably from –100 to 50° C., and particularly preferably from –90° C. to 30° C. and the reaction time is preferably from 0.5 to 30 hours, and particularly preferably from 1 to 18 hours.

The production of the heteroacene derivative of the formula (1) of the invention is preferably carried out in an inert atmosphere, such as nitrogen or argon.

In the process for producing the heteroacene derivative of the formula (1) of the invention, after the tetrahaloterphenyl derivative of the formula (2) is subjected to tetrametalation, the resulting product may be reacted with magnesium chloride and subsequently treated with the reaction agents represented by the formula (3) and the formula (4).

The thus obtained heteroacene derivative represented by the formula (1) of the invention can be further purified. The method for purification is not particularly limited and methods by column chromatography, recrystallization, or sublimation may be mentioned.

(Process for Producing Tetrahaloterphenyl Derivative)

The following will describe the process for producing the tetrahaloterphenyl derivative represented by the formula (2) which is used as a precursor for the heteroacene derivative represented by the formula (1) of the invention.

The tetrahaloterphenyl derivative represented by the formula (2) of the invention can be produced by reacting a tetrahalobenzene represented by the following formula (5) with 2-haloarylmetal reagents represented by the following formula (6) and the following formula (7) in the presence of a palladium catalyst and/or a nickel catalyst. In this connection, the reaction agents represented by the formula (6) and the formula (7) may be the same.

[Chem 19]

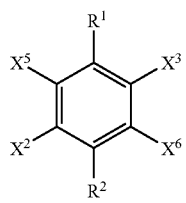

(5)

wherein the substituents $X^5$ and $X^6$ each represents a bromine atom, an iodine atom, or a chlorine atom; and the substituents $R^1, R^2, X^2$ and $X^3$ represent the same meanings as those of the substituents represented in the formula (2);

[Chem 20]

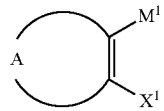

(6)

wherein $M^1$ represents a halide, a hydroxide, an alkoxide, or an alkylated product of magnesium, boron, zinc, tin, or silicone; the substituent $X^1$ and the ring A represent the same meanings as those of the substituent and the ring represented in the formula (2);

[Chem 21]

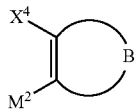

(7)

wherein $M^2$ represents a halide, a hydroxide, an alkoxide, or an alkylated product of magnesium, boron, zinc, tin, or silicone; and the substituent $X^4$ and the ring B represent the same meanings as those of the substituent and the ring represented in the formula (2).

The following will further describe the formulae (5), (6), and (7) of the invention.

The substituents $X^5$ and $X^6$ of the formula (5) represent a bromine atom, an iodine atom, or a chlorine atom, and preferred is a bromine atom or an iodine atom and more preferred is an iodine atom.

The substituents $R^1, R^2, X^2$ and $X^3$ represent the same meanings as those of the substituents represented by the formula (2).

As a specific compound represented by the formula (5), 1,4-dibromo-2,5-diiodobenzene is mentioned.

The substituents $M^1$ and $M^2$ in the formulae (6) and (7) each is a halide, a hydroxide, an alkoxide, or an alkylated product of magnesium, boron, zinc, tin, or silicone and is not particularly limited so far as it is a group which is eliminated by the above palladium and/or nickel catalyst and can be replaced by palladium and/or nickel. Examples thereof may include MgCl, MgBr, B(OH)$_2$, B(OMe)$_2$, a tetramethyldioxaboranyl group, ZnCl, ZnBr, ZnI, Sn(Bu-n)$_3$, and Si(Bu-n)$_3$ and preferred is ZnCl or B(OH)$_2$.

The substituents $X^1, X^4$ and the rings A, B represent the same meanings as those of the substituents and the rings represented in the formula (2).

Examples of specific compounds represented by the formula (6) and the formula (7) include 3-bromobenzothienyl-2-zinc chloride, 2-bromo-4,5-difluorophenylmagnesium bromide, 2-bromonaphthyl-3-magnesium bromide, 2-bromophenylbronic acid, and the like.

Incidentally, the 2-haloarylmetal reagent represented by the formula (6) or the formula (7) can be suitably prepared, for example, by performing a halogen/metal exchange reaction of an aryldihalogenated compound as a starting material thereof with a Grignard reagent such as isopropylmagnesium bromide or an organolithium reagent such as n-butyllithium, followed by reaction with zinc chloride, trimethoxyborane, or the like. In this connection, for the halogen/metal exchange reaction with a Grignard reagent, for example, a method described in "Journal of Organic Chemistry", 2006, vol. 65, pp. 4618-4634 can be also used and, for the halogen/metal exchange reaction with an organolithium reagent, for example, a method described in "Journal of Chemical Research Synopsis", 1981, p. 185 can be also used.

The catalyst for use in the reaction of the tetrahalobenzene represented by the formula (5) with the 2-haloarylmetal reagents represented by the formula (6) and the formula (7) is not particularly limited so far as it is a palladium and/or nickel catalyst. Examples thereof may include palladium chatalysts such as tetrakis(triphenylphosphine)palladium, a tris(dibenzylideneacetone)dipalladium/triphenylphosphine mixture, dichlorobis(triphenylphosphine)palladium, bis(tri-tert-butylphosphine)palladium, diacetatobis(triphenylphosphine) palladium, dichloro(1,2-bis(diphenylphosphino)ethane)palladium, a palladium acetate/triphenylphosphine mixture, a palladium acetate/tri-text-butylphosphine mixture, a palladium acetate/2-(dicyclohexylphosphino)-1,1'-biphenyl mixture, dichloro(ethylenediamine)palladium, dichloro(N,N,N',N'-tetramethylethylenediamine)palladium, and a dichloro(N,N,N',N'-tetramethylethylenediamine)-palladium/triphenylphosphine mixture; and nickel catalysts such as dichlorobis(triphenylphosphine)nickel, dichloro(1,2-bis(diphenylphosphino)ethane)nickel, dichloro(ethylenediamine)nickel, dichloro(N,N,N',N'-tetramethylethylenediamine)nickel, a dichloro(N,N,N',N'-tetramethylethylenediamine)nickel/triphenylphosphine mixture, and a bis(1,5-cyclooctadiene)nickel/triphenylphosphine mixture. Of these, a preferable catalyst is a zero valent palladium compound, and a particularly preferable catalyst is tetrakis(triphenylphosphine)-palladium. Moreover, these catalysts may be used singly or as a mixture of two or more thereof.

The reaction of the tetrahalobenzene represented by the formula (5) with the 2-haloarylmetal reagents represented by the formula (6) and the formula (7) in the presence of a palladium and/or nickel catalyst is preferably carried out in a solvent. The solvent to be used is not particularly limited and examples thereof are THF, diethyl ether, methyl tert-butyl ether, dioxane, ethylene glycol dimethyl ether, toluene, xylene, hexane, cyclohexane, ethanol, water, N,N-dimethylformamide, N-methylpyrrolidone, triethylamine, piperidine, pyrrolidine, diisopropylamine, and the like. Moreover, these solvents may be used singly or as a mixture of two or more thereof. For example, two or three component systems such as toluene/water, toluene/ethanol/water can be also used.

The amount of the palladium catalyst or nickel catalyst to be used is in the range of preferably 0.1 to 20% by mol, particularly preferably 1 to 10% by mol relative to the tetrahalobenzene represented by the formula (5).

The 2-haloarylmetal reagents of the formula (6) and the formula (7) can be used in the range of preferably 0.8 to 3.2 equivalents, particularly preferably 1.0 to 2.8 equivalents, and further preferably 1.1 to 2.5 equivalents to the tetrahalobenzene represented by the formula (5).

The temperature at the reaction is preferably from 10 to 120° C., particularly preferably from 30 to 100° C., and further preferably from 40 to 90° C. The reaction can be suitably carried out in the range of preferably 1 to 48 hours, and particularly preferably from 2 to 30 hours.

In this connection, a base may be present in the reaction system. In this case, the kind of the base is not particularly limited and examples thereof include inorganic bases such as sodium carbonate, sodium hydrogen carbonate, potassium carbonate, cesium carbonate, potassium phosphate, sodium phosphate, sodium tert-butoxide, and potassium fluoride; and organic bases such as triethylamine, trimethylamine, tributylamine, ethylenediamine, N,N,N',N'-tetramethylethylenediamine, diisopropylamine, and pyridine as suitable ones. The amount of the bases to be used is in the range of preferably 0.5 to 10.0 equivalents, and particularly preferably 2.0 to 8.0 equivalents to the tetrahalobenzene of the formula (5). Furthermore, in combination with these bases, a phase transfer catalyst may be also used. The kind of the phase transfer catalyst is not particularly limited and examples thereof may include trioctylmethylammonium chloride, tetrabutylammonium chloride, cetylpyridinium chloride, and the like as suitable ones. The amount of the phase transfer catalyst to be used is in the range of preferably 0.1 to 1.5 equivalents, and particularly preferably 0.2 to 0.8 equivalent to the tetrahalobenzene of the formula (5).

Furthermore, a phosphine such as triphenylphosphine may be also present in the reaction system. The amount of the phosphine to be used is in the range of preferably 0.9 to 8.0 equivalents, and particularly preferably 1.0 to 3.0 equivalents to the palladium and/or nickel catalyst.

In this connection, a copper compound may be present in the reaction system. The copper compound is not particularly limited and examples thereof may include monovalent copper compounds such as copper(I) chloride, copper(I) bromide, copper(I) iodide, and copper(I) acetate; divalent copper compounds such as copper(II) chloride, copper(II) bromide, copper(II) iodide, copper(II) acetate, and copper(II) acetylacetonate. Preferred is a monovalent copper compound, and particularly preferred is a copper(I) iodide. The amount of the copper compound to be used is in the range of preferably 0.3 to 10.0 equivalents, particularly preferably 0.6 to 6.0 equivalents to the palladium and/or nickel catalyst.

Moreover, the position where a carbon-carbon bond is formed by the reaction of the tetrahalobenzene represented by the formula (5) with the 2-haloarylmetal reagents represented by the formulae (6) and (7) can be controlled by the kind of the halogen.

Namely, since the reactivity of iodine is highest and the reactivity lowers in the order of bromine to chlorine, the position to be reacted can be arbitrarily determined by utilizing the reactivity depending on the kind of these halogens. Therefore, the production of the tetrahaloterphenyl derivative represented by the formula (2) can be achieved by arranging $X^5$ and $X^6$ in the formula (5) as iodine atoms and $X^2$ and $X^3$ as bromine atom(s) and/or chlorine atom(s).

The thus obtained tetrahaloterphenyl derivative represented by the formula (2) of the invention can be further purified. The method for purification is not particularly limited and methods by column chromatography, recrystallization, or sublimation may be mentioned.

(Oxidation-Resistant Organic Semiconductor Material)

The following will describe the oxidation-resistant organic semiconductor material containing the heteroacene derivative represented by the formula (1) of the invention. The oxidation-resistant organic semiconductor material is excellent in solubility in a solvent and oxidation resistance and has a suitable coating ability. The oxidation-resistant organic semiconductor material can be produced by dissolving the heteroacene derivative represented by the formula (1) of the invention in a solvent.

The solvent for use in dissolution of the heteroacene derivative represented by the formula (1) of the invention is not particularly limited and examples thereof include halogen-based solvents such as o-dichlorobenzene, chlorobenzene, 1,2-dichloroethane, 1,1,2,2-tetrachloroethane, and chloroform; ether-based solvents such as THF and dioxane; hydrocarbon-based solvents such as aromatic compounds including toluene, xylene, and mesitylene; ester-based solvents such as ethyl acetate and γ-butyrolactone; amide-based solvents such as N,N-dimethylformamide and N-methylpyrrolidone; and the like. These solvents may be used singly or as a mixture of two or more thereof. Of these, preferred is chlorobenzene, toluene, or the like.

By mixing the solvent mentioned in the above and the heteroacene derivative represented by the formula (1) and stirring the mixture, the oxidation-resistant organic semiconductor material containing the heteroacene derivative represented by the formula (1) is formed. The temperature at the mixing and stirring is preferably from 10 to 200° C., and particularly preferably from 20° C. to 190° C. The concentration of the heteroacene derivative represented by the formula (1) at the mixing and stirring can be varied by the solvent and temperature and is preferably from 0.01 to 10.0% by weight. The preparation of the solution can be carried out even in the air and preferably under an inert atmosphere, such as nitrogen or argon.

The evaluation of the oxidation resistance of the oxidation-resistant organic semiconductor material containing the heteroacene derivative represented by the formula (1) can be carried out by the method of bringing the solution into contact with air for a predetermined period of time. First, the solvent to be used is degassed beforehand to remove dissolved oxygen. The contact period with air is suitably selected depending on the temperature and is preferably from 0.5 minute to 3 hours. The proceeding of oxidation can be confirmed by observing color change of the solution and detecting oxidation products by gas chromatography and gas chromatography (GC)-mass spectrometry (GCMS) analysis.

The oxidation-resistant organic semiconductor material containing the heteroacene derivative represented by the formula (1) of the invention is suitably applied to the production of the organic thin film by a coating process, since the heteroacene derivative represented by the formula (1) itself to be used has an appropriate cohesiveness, can be dissolved in a solvent at relatively low temperature, and has oxidation resistance. Namely, since air is not necessarily strictly removed from the atmosphere, the coating step can be simplified. The coating can be carried out even in the air and preferably under a nitrogen atmosphere when drying of the solvent is considered. In order to obtain suitable coating ability, the viscosity of the oxidation-resistant organic semiconductor material containing the heteroacene derivative represented by the formula (1) of the invention is preferably in the range of 0.005 to 20 poise.

(Organic Thin Film)

The following will describe the organic thin film wherein the oxidation-resistant organic semiconductor material containing the heteroacene derivative represented by the formula (1) of the invention is used. Such an organic thin film can be produced by recrystallization of the above oxidation-resistant organic semiconductor material (solution) or coating a substrate therewith. Particularly, it is preferred to produce the film by coating a substrate. By production through coating a substrate therewith, an organic thin film formed on the substrate is prepared.

The thin film by recrystallization can be formed by cooling the above oxidation-resistant organic semiconductor material. The atmosphere at the time when the organic thin film is produced is preferably an inert gas such as nitrogen, argon or air and particularly preferably under an inert gas such as nitrogen or argon. The concentration of the heteroacene derivative represented by the formula (1) in the solution is not particularly limited and is, for example, from 0.01 to 10.0% by weight. The cooling can be suitably carried out by cooling the solution preferably from a temperature of 60 to 200° C. to a temperature of −20° to 60° C., particularly preferably −10° C. to 40° C. Also, thus produced crystalline organic thin film can be attached on an appropriate substrate, that is, production on the substrate can be conducted by lamination or the like. The film thickness of the thin film obtained by recrystallization is not particularly limited and is preferably from 50 nm to 2 mm, particularly preferably from 1 to 500 μm.

The production of the organic thin film by coating a substrate can be carried out by applying the above oxidation-resistant organic semiconductor material on the substrate and subsequently vaporizing the solvent by heating, air-stream, natural drying, and the like method. The concentration of the heteroacene derivative represented by the formula (1) in the solution is not particularly limited and is preferably from 0.01 to 10.0% by weight, for example. The coating temperature is not particularly limited and the coating can be suitably carried out between 20° C. and 200° C. A specific method for coating is not particularly limited and known methods such as spin coating, cast coating, dip coating, and the like can be used. Furthermore, printing technologies such as screen printing, inkjet printing, gravure printing can be also used for the production. The material for the substrate to be used is not particularly limited and various crystalline or non-crystalline materials can be used. As specific examples, there may be suitably used substrates of plastics such as polyethylene terephthalate, polymethyl methacrylate, polyethylene, polypropylene, polystyrene, cyclic polyolefins, polyimides, polycarbonates, polyvinylphenol, polyvinyl alcohol, poly(diisopropyl fumalate), poly(diethyl fumarate), and poly(diisopropyl maleate); substrates of inorganic materials such as glass, quarts, aluminum oxide, silicon, silicon oxide, tantalum dioxide, tantalum pentoxide, and indium tin oxide; substrates of metals such as gold, copper, chromium, and titanium. Moreover, there can be used substrates whose surface is modified with a silane such as octadecyltrichlorosilane or octadecyltrimethoxysilane or a silylamine such as hexamethyldisilazane. Furthermore, the substrate may be a insulating or dielectric material. The solvent after coating can be removed for drying under normal pressure or reduced pressure. Alternatively, the solvent may be removed for drying by heating or nitrogen stream. Furthermore, by regulating the vaporization rate of the solvent, crystal growth of the heteroacene derivative represented by the formula (1) of the invention can be controlled. The film thickness of the thin film obtained by coating the substrate is not particularly limited and is preferably from 1 nm to 100 μm, particularly preferably from 10 nm to 20 μm.

The heteroacene derivative represented by the formula (1) of the invention has a molecular structure with high plane rigidity, so that it is expectable to provide excellent semiconductor properties. Moreover, the heteroacene derivative dissolves in a solvent such as toluene or chlorobenzene and is not easily oxidized with air even in a solution state. Therefore, a semiconductor thin film can be easily formed by a coating process. Thus, the heteroacene derivative represented by the formula (1) of the invention can be utilized in electronic materials for uses as an organic semiconductor active phase of transistor for electronic papers, organic EL displays, liquid crystal displays, IC tags, or the like; an organic EL display material; an organic semiconductor laser material; an organic thin film solar battery material; a photonic crystalline material, or the like.

EXAMPLES

The following will describe the invention further in detail with reference to Examples but the invention is not limited to these Examples.

For identification of products, $^1$H-NMR spectra and mass spectra were used. The $^1$H-NMR spectra were measured using JEOL GSX-270WB (270 MHz) manufactured by JEOL Ltd. The mass spectra were measured using JEOL JMS-700 manufactured by JEOL Ltd. by an electron impact (EI) method (70 eV) or a FAD method (6 keV, xenon gas, matrix (dithiothreitol:dithioerythritol=3:1)) (FABMS) with direct introduction of a sample.

For confirmation of the progress of a reaction, analyses on gas chromatography (GC) and gas chromatography-mass spectroscopy (GCMS) were employed.

Analysis on Gas Chromatography
  Apparatus: Shimadzu GC14B
  Column: DB-1 manufactured by J & W Scientific Co. Ltd., 30 m
Analysis on Gas Chromatography-Mass Spectroscopy
  Apparatus: Perkin-Elmer autosystem XL (MS portion: turbo mass gold)
  Column: DB-1 manufactured by J & W Scientific Co. Ltd., 30

As the reagents and solvents for reactions, commercially available products were used unless otherwise stated. In the case where an organometallic reagent such as a Grignard reagent or butyllithium was used, a commercially available anhydrous solvent was used as it was.

Synthetic Example 1

Synthesis of 1,4-Dibromo-2,5-diiodobenzene)

1,4-Dibromo-2,5-diiodobenzene was synthesized with reference to the method described in Journal of American Chemical Society, 1997, vol. 119, pp. 4578-4593.

To a 1 L three-necked flask fitted with a mechanical stirrer were added 16.7 g (73.0 mmol) of periodic acid and 525 ml of sulfuric acid. After periodic acid was dissolved, 36.4 g (219 mmol) of potassium iodide was added portionwise. The content was cooled to a temperature of −30° C. and 34.5 g (146 mmol) of 1,4-dibromobenzene was added over a period of 5 minutes. The resulting mixture was stirred at −25° C. for 36 hours. After the reaction mixture was poured into ice (2 kg), the whole was filtrated and a solid was taken out. The solid was dissolved in chloroform, the solution was washed with a 5% aqueous sodium hydroxide solution and water, and the organic phase was dried over anhydrous magnesium sulfate. After concentration under reduced pressure, the residue was recrystallized from chloroform to obtain white crystals (36.0 g, yield 50%).

$^1$H-NMR (CDCl$_3$, 21° C.): δ=8.02 (s, 2H).

Since $^1$H-NMR spectrum thereof was coincident with that in literature, it was confirmed that 1,4-dibromo-2,5-diiodobenzene was obtained.

Synthetic Example 2

Synthesis of 2-Phenyl-5-bromo-4-biphenylboronic Acid

1) Synthesis of 1,2-Dibromo-4,5-diiodobenzene 1,2-Dibromo-4,5-diiodobenzene was synthesized in accordance with "Synlett", 2003, pp. 29-34.

To a 1 L three-necked flask fitted with a mechanical stirrer were added 36.9 g (162 mmol) of periodic acid and 150 ml of sulfuric acid. After periodic acid was dissolved, 80.7 g (486 mmol) of potassium iodide was added portionwise. The content was cooled to a temperature of 0° C. and 75.0 g (318 mmol) of 1,2-dibromobenzene was added. The resulting mixture was stirred at 0° C. for 30 minutes. After the reaction mixture was poured into ice, the whole was filtrated and a solid was taken out. The solid was recrystallized twice from THF/methanol to obtain white crystals (76.2 g, yield 49%).

$^1$H-NMR (CDCl$_3$, 21° C.) δ=8.03 (s, 2H).

From the $^1$H-NMR measurement, it was confirmed that 1,2-dibromo-4,5-diiodobenzene was obtained.

2) Synthesis of 1,2-Dibromo-4,5-diphenylbenzene

To a 200 ml Schlenk reaction vessel were added under a nitrogen atmosphere 3.074 g (6.30 mmol) of 1,2-dibromo-4,5-diiodobenzene synthesized in 1), 600 mg (0.519 mmol) of tetrakis(triphenylphosphine)palladium (manufactured by Tokyo Chemical Industry Co. Ltd.), and 1.920 g (15.7 mmol) of phenylboronic acid (manufactured by Wako Pure Chemical Industries, Ltd.). Further, 50 ml of toluene, 13 ml of ethanol, and an aqueous solution composed of 4.007 g (37.8 mmol) of sodium carbonate and 16 ml of water were added. The whole was heated to 82° C. and stirred for 24 hours. After cooling to room temperature, toluene and water were added and phase separation was conducted. The organic phase was concentrated and the resulting residue was dissolved in 26 ml of toluene. Thereafter, 1.0 ml of a 70% tert-butyl hydroperoxide solution (manufactured by Wako Pure Chemical Industries, Ltd.) was added, followed by 2 hours of stirring at room temperature. After the toluene solution was washed twice with water, the organic phase was concentrated under reduced pressure and the resulting residue was purified by silica gel column chromatography (solvent, hexane) to obtain a white solid (1.953 g, yield 80%).

$^1$H-NMR (CDCl$_3$, 21° C.): δ=7.67 (s, 2H), 7.24-7.13 (m, 6H), 7.12-6.90 (m, 4H).

MS m/z: 388 (M$^+$, 100%), 308 (M$^+$-Br, 23), 228 (M$^+$-Br, 53).

From the $^1$H-NMR measurement and the MS measurement, it was confirmed that 1,2-dibromo-4,5-diphenylbenzene was obtained.

3) Synthesis of 2-Phenyl-5-bromo-4-biphenylboronic Acid

To a 100 ml Schlenk reaction vessel were added under a nitrogen atmosphere 755 mg (1.95=mol) of 1,2-dibromo-4,5-diphenylbenzene synthesized in 2) and 12 ml of THF. The solution was cooled to −100° C. and 1.3 ml (2.1 mmol) of a hexane solution of n-butyllithium (manufactured by Kanto Chemical Co., Ltd., 1.59M) was added dropwise. After 30 minutes of aging, 472 my (2.51 mmol) of triisopropyl borate (manufactured by Tokyo Chemical Industry Co., Ltd.) was added dropwise. After the temperature was gradually raised to room temperature, 3N hydrochloric acid was added and phase separation was conducted. The organic phase was concentrated under reduced pressure to obtain 770 my of a white solid (2-phenyl-5-bromo-4-biphenylboronic acid).

Synthetic Example 3

Synthesis of 2-Bromo-3-iodonaphthalene

2-Bromo-3-iodonaphthalene was synthesized with reference to the method described in Synthetic Communications, 2003, vol. 33, pp. 2751-2756. A starting material, 2-bromo-bis(hexachlorocyclopentadiene)-naphthalene was purchased from Sigma-Aldrich and used as it was.

To a 500 ml three-necked flask reaction vessel were added under a nitrogen atmosphere 200 ml of methanesulfonic acid and 1.31 g (5.74 mmol) of orthoperiodic acid. After 30 minutes of stirring, 4.36 g (17.2 mmol) of iodine was added thereto. After the mixture was stirred for 2 hours, 30.1 g (40.0 mmol) of 2-bromo-bis(hexachlorocyclopentadiene)naphthalene was added portionwise. The mixture was stirred at 30° C. for 3 days. The reaction mixture was poured into ice water and the formed solid was filtrated. The solid was further washed with water and dried under reduced pressure to obtain a white powder of 2-bromo-3-iodo-bis(hexachlorocyclopentadiene) naphthalene (34.8 g, yield 99%).

To a terminal end of a glass sublimation tube was added 8.05 g (9.16 mmol) of 2-bromo-3-iodo-bis(hexachlorocyclopentadiene)naphthalene obtained in the above. The terminal end was heated to 210° C. and the pressure was reduced to 1.5 Pa. The generated 2-bromo-3-iodonaphthalene attached to the glass tube at a reduced pressure side and hexachlorocyclopentadiene was collected at the bottom of the reduced pressure side. After 1 hour, the sublimation operation was stopped, the attached matter on the glass tube was taken out, and then the same operation was again repeated. The sublimation operation was continued for 1 hour (2.29 g, yield 75%).

$^1$H-NMR (CDCl$_3$, 21° C.): δ=8.41 (s, 1H), 8.14 (s, 1H), 7.75-7.65 (m, 2H), 7.54-7.45 (m, 2H).

Since $^1$H-NMR spectrum thereof was coincident with that in literature, it was confirmed that 2-bromo-3-iodonaphthalene was obtained.

Example 1

Synthesis of {1,4-Bis(3-bromobenzothienyl)-2,5-dibromo}benzene (tetrahaloterphenyl derivative))

To a 100 ml Schlenk reaction vessel were added under a nitrogen atmosphere 886 mg (3.03 mmol) of 2,3-dibromobenzothiophene (manufactured by Sigma-Aldrich) and 8 ml of THF. The solution was cooled to −30° C. and 3.8 ml (3.0 mmol) of a THF solution of isopropylmagnesium bromide (manufactured by Tokyo Chemical Industry Co. Ltd., 0.80M) was added dropwise. After 30 minutes of aging, the whole was cooled to −50° C. and 3.0 ml (3.0 mmol) of a diethyl ether solution of zinc chloride (manufactured by Sigma-Aldrich, 1.0M) was added dropwise at the temperature. After the temperature was gradually raised to room temperature, the formed white slurry liquid was concentrated under reduced pressure. To the obtained white solid [(3-bromobenzothienyl-2-zinc chloride) (compound of the formulae (6) and (7))] were added 492 mg (1.01 mmol) of 1,4-dibromo-2,5-diiodobenzene synthesized in Synthetic Example 1 (compound of the formula (5)), 91.7 mg (0.079 mmol) of tetrakis(triphenylphosphine)palladium (manufactured by Tokyo Chemical Industry Co. Ltd.) as a catalyst, and 8 ml of THF. After the reaction was carried out at 63° C. for 10 hours, the vessel was cooled with water and the reaction was stopped by adding 4 ml of 1N hydrochloric acid. Toluene was added, the obtained suspension was filtrated, and the solid on the filter plate was washed with toluene and water. The solid was dried under reduced pressure to obtain 292 mg of a white solid. On the other hand, the filtrate was subjected to phase separation and the organic phase was washed with water. The organic phase was concentrated under reduced pressure and the solvent was removed by evaporation. The obtained solid was washed with hexane (10 ml) and the residue was recrystallized from toluene. After the precipitated crystals were dried under reduced pressure, 206 mg of a white solid was obtained. The objective product was obtained in 75% yield together with the white solid after the previous filtration.

$^1$H-NMR (CDCl$_3$, 21° C.): δ=7.95-7.84 (m, 4H), 7.81 (s, 2H), 7.58-7.44 (m, 4H).

MS m/z: 658 (M$^+$, 44%), 498 (M$^+$-2Br, 34), 338 (M$^+$-4Br, 100), 306 (M$^+$-4Br—S), 9), 169 (M$^+$-4Br)/2, 66).

From the $^1$H-NMR measurement and the MS measurement, it was confirmed that {1,4-bis(3-bromobenzothienyl)-2,5-dibromo}benzene was obtained. The following shows its structural formula.

[Chem 22]

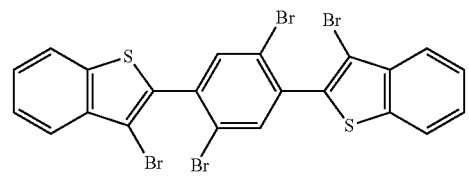

Example 2

Synthesis of Tetrathienoacene (Heteroacene Derivative)

To a 100 ml Schlenk reaction vessel were added under a nitrogen atmosphere 422 mg (0.641 mmol) of {1,4-bis(3-bromobenzothienyl)-2,5-dibromo}benzene synthesized in Example 1 and 30 ml of THF. The solution was cooled to −75° C. and 5.1 ml (5.1 mmol) of a cyclohexane/hexane solution of sec-butyllithium (manufactured by Kanto Chemical Co., Ltd., 1.0M) was added dropwise as a metalation agent to effect tetrametalation. After 40 minutes of stirring, 730 mg (2.32 mmol) of bis(phenylsulfonyl)sulfide (manufactured by Across) (compound of the formulae (3) and (4)) was charged at once at −70° C. as a reaction agent and the temperature was raised to room temperature over a period of overnight. A saturated aqueous sodium chloride solution was added, then phase separation was conducted, and the organic phase was washed with a saturated aqueous sodium chloride solution. Since the organic phase was a yellow suspension, it was filtrated to collect a yellow solid, which was dried under reduced pressure to obtain 123 mg of a yellow solid. The formed solid was filtrated. Further, after the obtained solid was extracted with o-dichlorobenzene (50° C.), the extract was dried under reduced pressure. The residue was washed with toluene at 60° C. and the residue was dried under reduced pressure to obtain a yellow solid (71 mg, yield 28%).

MS m/z: 402 (M$^+$, 100%), 201 (M$^+$/2, 14).

From the MS measurement, it was confirmed that tetrathienoacene was obtained. The following shows its structural formula.

[Chem 23]

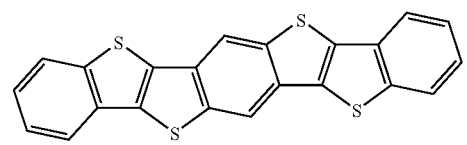

Example 3

Synthesis of 2,2',5',2''-tetrabromo-1,1',4',1''-terphenyl (tetrahaloterphenyl derivative)

To a 100 ml Schlenk reaction vessel were added under a nitrogen atmosphere 4.39 g (9.00 mmol) of 1,4-dibromo-2,5-diiodobenzene (compound of the formula (5)) synthesized in Synthetic Example 1, 974 mg (0.84 mmol) of tetrakis (triphenylphosphine)palladium (manufactured by Tokyo Chemical Industry Co. Ltd.) as a catalyst, and 4.16 g (20.7 mmol) of 2-bromophenylboronic acid (manufactured by Sigma-Aldrich) (compound of the formulae (6) and (7)). Further, 72 ml of toluene, 18 ml of ethanol, and an aqueous solution composed of 5.72 g (54.0 mmol) of sodium carbonate and 22 ml of water were added. The whole was immersed in an oil bath at 85° C. and stirred for 15 hours. After cooling to room temperature, dichloromethane and a saturated aqueous sodium chloride solution were added and phase separation was conducted. The organic phase was concentrated under reduced pressure. The residue was recrystallized from toluene to obtain white needle-like crystals (3.68 g, yield 75%).

Melting point: 230-231° C.

$^1$H-NMR (CDCl$_3$, 21° C.): δ=7.70 (d, J=8.0 Hz, 2H), 7.55 (d, J=1.5 Hz, 2H), 7.45-7.23 (m, 6H).

MS m/z; 546 (M$^+$, 92%), 466 (M$^+$-Br, 45), 386 (M$^+$-2Br, 53), 226 (M$^+$-4Br, 100).

From the $^1$H-NMR measurement and the MS measurement, it was confirmed that 2,2',5',2"-tetrabromo-1,1',4',1"-terphenyl was obtained. The following shows its structural formula.

[Chem 24]

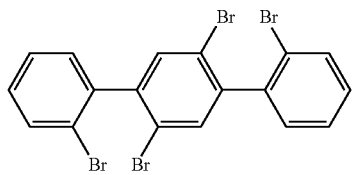

Example 4

Synthesis of P,P-diphenylbenzophospholodibenzophosphole (Heteroacene Derivative)

To a 100 ml Schlenk reaction vessel were added under a nitrogen atmosphere 410 mg (0.752 mmol) of 2,2',5',2"-tetrabromo-1,1',4',1"-terphenyl synthesized in Example 3 and 30 ml of THF. The solution was cooled to −80° C. and 6.0 ml (6.0 mmol) of a cyclohexane/hexane solution of sec-butyllithium (manufactured by Kanto Chemical Co, Ltd., 1.0M) was added dropwise as a metalation agent to effect tetrametalation. The color of the solution changed from light yellow to true green. After 20 minutes of stirring, 452 mg (2.52=mol) of dichlorophenylphosphine (manufactured by Tokyo Chemical Industry Co. Ltd.) (compound of the formulae (3) and (4)) was charged at −75° C. as a reaction agent and the temperature was raised to room temperature over a period of overnight. A saturated aqueous sodium chloride solution was added, then phase separation was conducted, and the organic phase was washed with an aqueous potassium carbonate solution. After concentration under reduced pressure, hexane was added to the resulting residue and, after stirring, the whole was allowed to stand. The supernatant was removed and the residue was dried under reduced pressure. The residue was recrystallized from toluene to obtain pale yellow crystals (101 mg, yield 30%).

$^1$H-NMR (CDCl$_3$, 21° C.): δ=8.26 (s, 2H), 7.94 (d, J=7.8 Hz, 2H), 7.69 (d, J=7.1 Hz, 2H), 7.44 (t, J=7.8 Hz, 2H), 7.41-7.10 (m, 12H).

MS m/z: 442 (M$^+$, 100%), 364 (M$^+$-Ph-1, 38), 288 (M$^+$-2Ph, 19), 221 (M$^+$/2, 10).

From the $^1$H-NMR measurement and the MS measurement, it was confirmed that P,P-diphenylbenzophospholodibenzophosphole was obtained. The following shows its structural formula.

[Chem 25]

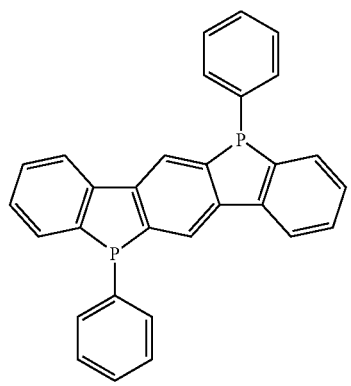

Example 5

Synthesis of B,B-diphenylbenzoborolyldibenzoborole (Heteroacene Derivative)

To a 100 ml Schlenk reaction vessel were added under a nitrogen atmosphere 425 mg (0.778 mmol) of 2,2',5',2"-tetrabromo-1,1',4',1"-terphenyl synthesized in Example 3 and 30 ml of THF. The solution was cooled to −80° C. and 6.2 ml (6.2 mmol) of a cyclohexane/hexane solution of sec-butyllithium (manufactured by Kanto Chemical Co., Ltd., 1.0M) was added dropwise as a metalation agent to effect tetrametalation. The color of the solution changed from light yellow to true green. After 20 minutes of stirring, 410 mg (2.58 mmol) of dichlorophenylborane (manufactured by Sigma-Aldrich) (compound of the formulae (3) and (4)) was charged at −75° C. as a reaction agent and the temperature was raised to room temperature over a period of overnight. A saturated aqueous sodium chloride solution was added, then phase separation was conducted, and the organic phase was washed with an aqueous potassium carbonate solution. After concentration under reduced pressure, hexane was added to the resulting residue and, after stirrings the whole was allowed to stand. The supernatant was removed and the residue was dried under reduced pressure. The residue was recrystallized from toluene to obtain pale yellow crystals (78 mg, yield 25%).

MS m/z: 402 (M$^+$, 100%), 201 (M$^+$/2, 14).

From the MS measurement, it was confirmed that B,B-diphenylbenzoborolyldibenzoborole was obtained. The following shows its structural formula.

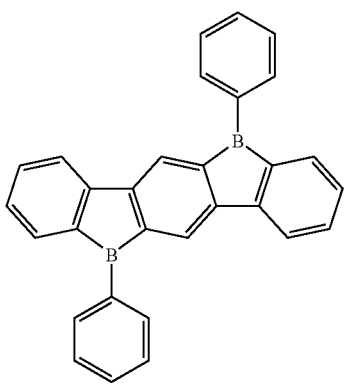

Example 6

Synthesis of 4,5,4",5"-Tetrafluoro-2,2',5',2"-tetrabromo-1,1',4',1"-terphenyl(tetrahaloterphenyl derivative)

To a 100 ml Schlenk reaction vessel were added under a nitrogen atmosphere 2.53 g (9.30 mmol) of 1,2-dibromo-4,5-difluorobenzene (manufactured by Wako Pure Chemical Industries, Ltd.) and 15 ml of THF. The solution was cooled to −40° C. and 15 ml (9.7 mmol) of a THF solution of isopropylmagnesium bromide (manufactured by Kanto Chemical Co., Ltd., 0.65M) was added dropwise. After 30 minutes of aging, 9.8 ml (9.8 mmol) of a diethyl ether solution of zinc chloride (manufactured by Sigma-Aldrich, 1.0M) was added dropwise at the temperature. After the temperature was gradually raised to room temperature, the formed white slurry liquid was concentrated under reduced pressure. To the resulting white solid (2-bromo-4,5-difluorophenylmagnesium bromide) (compound of the formulae (6) and (7)) were added 2.15 g (4.41 mmol) of 1,4-dibromo-2,5-diiodobenzene synthesized in Synthetic Example 1 (compound of the formula (5)), 408 mg (0.353 mmol) of tetrakis(triphenylphosphine)palladium (manufactured by Tokyo Chemical Industry Co. Ltd.), and 30 ml of THF. After the reaction was carried out at 60° C. for 6 hours, the vessel was cooled with water and the reaction was stopped by adding 3N hydrochloric acid (8 ml). After toluene and sodium chloride were added, then phase separation was conducted, and the organic phase was washed with an aqueous sodium chloride solution. The organic phase was concentrated under reduced pressure and the solvent was removed by distillation. The obtained residue was dissolved in 10 ml of toluene and a 70% tert-butyl hydroperoxide solution (manufactured by Wako Pure Chemical Industries, Ltd.) (0.5 ml) was added, followed by 2 hours of stirring at room temperature. The solution was washed with water and the organic phase was concentrated under reduced pressure. The organic phase was dissolved in toluene:hexane=1:1 and was passed through a column packed with silica gel. The elute was concentrated under reduced pressure and the resulting solid was recrystallized using a mixed solvent of hexane:toluene=3:1 to obtain a white solid (1.48 g, yield 54%).

$^1$H-NMR (CDCl$_3$, 21° C.): δ=7.58-7.45 (m, 2H), 7.53 (s, 2H), 7.23-7.09 (m, 2H).

MS m/z; 618 (M$^+$, 73%), 538 (M$^+$-Br, 32), 458 (M$^+$-2Br, 45), 378 (M$^+$-3Br, 4), 298 (M$^+$-4Br, 100).

From the $^1$H-NMR measurement and the MS measurement, it was confirmed that 4,5,4",5"-tetrafluoro-2,2',5',2"-tetrabromo-1,1',4',1"-terphenyl was obtained. The following shows its structural formula.

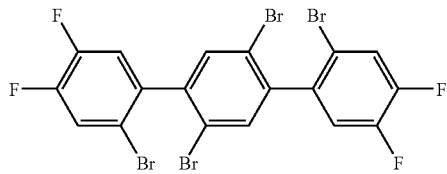

Example 7

Synthesis of Tetrafluorodithienoacene (Heteroacene Derivative)

To a 100 ml Schlenk reaction vessel were added under a nitrogen atmosphere 506 mg (0.818 mmol) of 4,5,4",5"-tetrafluoro-2,2',5',2"-tetrabromo-1,1',4',1"-terphenyl synthesized in Example 6 and 28 ml of THF. The suspension solution was cooled to −80° C. and 5.9 ml (5.9 mmol) of a cyclohexane/hexane solution of sec-butyllithium (manufactured by Kanto Chemical Co., Ltd., 1.0M) was added dropwise as a metalation agent to effect tetrametalation. After 20 minutes of stirring, 900 mg (2.86 mmol) of bis(phenylsulfonyl)sulfide (manufactured by Across) (compound of the formulae (3) and (4)) was charged at once at −75° C. and the temperature was gradually raised to room temperature over a period of overnight. A saturated aqueous sodium chloride solution and toluene were added, then phase separation was conducted, and the organic phase was washed with an aqueous sodium chloride solution. After concentration under reduced pressure, hexane was added to the resulting residue and, after stirring, the whole was allowed to stand. The supernatant was removed and the residue was dried under reduced pressure. The residue was recrystallized from toluene (77 mg, yield 26%).

$^1$H-NMR (CDCl$_3$, 21° C.): δ=8.46 (s, 2H), 8.10 (m, 2H), 7.81 (m, 2H).

MS m/z: 362 (M$^+$, 100%), 181 (M$^+$/2, 18)

From the $^1$H-NMR measurement and the MS measurement, it was confirmed that tetrafluorodithienoacene was obtained. The following shows its structural formula.

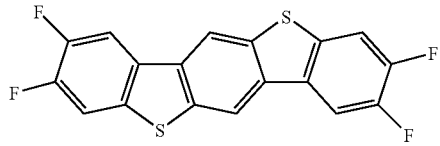

Example 8

Synthesis of 4,5,4",5"-Tetraphenyl-2,2',5',2"-tetrabromo-1,1',4',1"-terphenyl (tetrahaloterphenyl derivative)

To a 100 ml Schlenk reaction vessel were added under a nitrogen atmosphere 770 mg of 2-phenyl-5-bromo-4-biphenylboronic acid synthesized in Synthetic Example 2 (compound of the formulae (6) and (7)), 476 mg (0.976 mmol) of 1,4-dibromo-2,5-diiodobenzene synthesized in Synthetic Example 1 (compound of the formula (5)), 90.1 mg (0.078 mmol) of tetrakis(triphenylphosphine)palladium (manufactured by Tokyo Chemical Industry Co. Ltd.), 7.6 ml of toluene, and 1.8 ml of ethanol. Further, a solution composed of 625 mg (5.90 mmol) of sodium carbonate and 2.3 ml of water was added and the resulting mixture was subjected to a reaction at 85° C. for 30 hours. After cooling to room temperature, toluene and an aqueous sodium chloride solution were added and phase separation was conducted. The organic phase was washed with an aqueous sodium chloride solution. The organic phase was concentrated under reduced pressure and the solvent was removed by distillation. The resulting solid was recrystallized using a mixed solvent of toluene:hexane=7:3 to obtain a white solid (467 mg, yield 56%).

$^1$H-NMR (CDCl$_3$, 21° C.) δ=7.77 (s, 0.85H), 7.76 (s, 1.15H) 7.69 (s, 2H), 7.42 (s, 1.15H), 7.35 (s, 0.85H), 7.28-7.13 (m, 20H).

FABMS m/z: 850 (M$^+$, 100%), 770 (M$^+$-Br, 71).

From the $^1$H-NMR measurement and the FABMS measurement, it was confirmed that 4,5,4'',5''-tetraphenyl-2,2',5',2''-tetrabromo-1,1',4',1''-terphenyl was obtained. The following shows its structural formula.

[Chem 29]

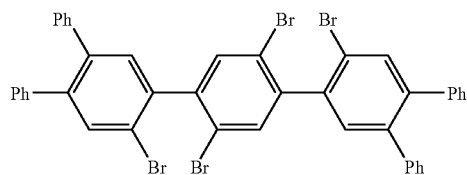

Example 9

Synthesis of Tetraphenyldithienoacene (Heteroacene Derivative)

To a 100 ml Schlenk reaction vessel were added under a nitrogen atmosphere 416 mg (0.489 mmol) of 4,5,4'',5''-tetraphenyl-2,2',5',2''-tetrabromo-1,1',4',1''-terphenyl synthesized in Example 8 and 30 ml of THF. The suspension solution was cooled to –80° C. and 3.9 ml (3.9 mmol) of a cyclohexane/hexane solution of sec-butyllithium (manufactured by Kanto Chemical Co., Ltd., 1.0M) was added dropwise as a metalation agent to effect tetrametalation. After 20 minutes of stirring, 507 mg (1.61 mmol) of bis(phenylsulfonyl)sulfide (manufactured by Across) (compound of the formulae (3) and (4)) was charged at once at –75° C. and the temperature was gradually raised to room temperature over a period of overnight. A saturated aqueous sodium chloride solution and toluene were added, then phase separation was conducted, and the organic phase was washed with an aqueous sodium chloride solution. After concentration under reduced pressure, hexane was added to the resulting residue and, after stirring, the whole was allowed to stand. The supernatant was removed and the residue was dried under reduced pressure. The residue was recrystallized from toluene to obtain crystals (90 mg, yield 31%).

MS m/z: 594 (M$^+$, 100%), 297 (M$^+$/2, 15)

From the MS measurement, it was confirmed that tetraphenyldithienoacene was obtained. The following shows its structural formula.

[Chem 30]

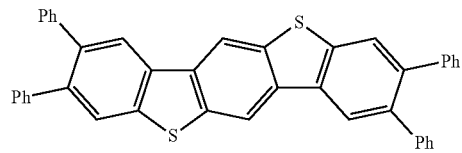

Example 10

Synthesis of 2,2',5',2''-Tetrabromo-1,1',4',1''-dibenzoterphenyl (tetrahaloterphenyl derivative)

To a 100 ml Schlenk reaction vessel were added under a nitrogen atmosphere 2.03 g (6.10 mmol) of 2-bromo-3-iodonaphthalene synthesized in Synthetic Example 3 and 12 ml of THF. The solution was cooled to –65° C. and 9.9 ml (6.4 mmol) of a THF solution of isopropylmagnesium bromide (manufactured by Kanto Chemical Co., Ltd., 0.65M) was added dropwise. After 30 minutes of aging, 6.4 ml (6.4 mmol) of a diethyl ether solution of zinc chloride (manufactured by Sigma-Aldrich, 1.0M) was added dropwise at the temperature. After the temperature was gradually raised to room temperature, the formed white slurry liquid was concentrated under reduced pressure. To the obtained white solid (2-bromonaphthyl-3-magnesium bromide) (compound of the formulae (6) and (7)) were added 1.41 g (2.88 mmol) of 1,4-dibromo-2,5-diiodobenzene synthesized in Synthetic Example 1 (compound of the formula (5)), 285 mg (0.247 mmol) of tetrakis(triphenylphosphine)palladium (manufactured by Tokyo Chemical Industry Co. Ltd.), and 31 ml of THF. After the reaction was carried out at 60° C. for 4 hours, the vessel was cooled with water and the reaction was stopped by adding 4 ml of 3N hydrochloric acid. The whole was concentrated under reduced pressure and the solvent was removed by distillation. The precipitated solid was washed with water until the filtrate showed neutral and further washed with chloroform and THF. The resulting crystals were dried under reduced pressure to obtain crystals (1.20 g, yield 64%).

$^1$H-NMR (CDCl$_3$, 60° C.): δ=8.22 (s, 2H), 7.90-7.75 (m, 4H), 7.85 (s, 2H), 7.67 (s, 2H), 7.60-7.48 (m, 4H).

MS m/z: 646 (M$^+$, 64%), 566 (M$^+$-Br, 8), 486 (M$^+$-2Br, 34), 406 (M$^+$-3Br, 6), 326 (M$^+$-4Br, 92), 163 ((M$^+$-4Br)/2, 100).

From the $^1$H-NMR measurement and the MS measurement, it was confirmed that 2,2',5',2''-tetrabromo-1,1',4',1''-dibenzoterphenyl was obtained. The following shows its structural formula.

[Chem 31]

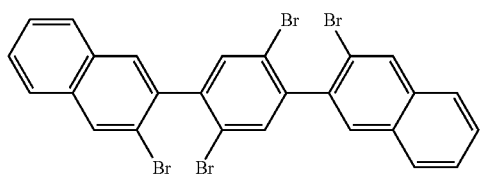

Example 11

Synthesis of Dibenzodithienoacene (Heteroacene Derivative)

To a 100 ml Schlenk reaction vessel were added under a nitrogen atmosphere 388 mg (0.601 mmol) of 2,2',5',2''-tetrabromo-1,1',4',1''-dibenzoterphenyl synthesized in Example 10 and 27 ml of THF. The suspension solution was cooled to −80° C. and 4.8 ml (4.8 mmol) of a cyclohexane/hexane solution of sec-butyllithium (manufactured by Kanto Chemical Co., Ltd., 1.0M) was added dropwise as a metalation agent to effect tetrametalation. After 20 minutes of stirring, 660 mg (2.10 mmol) of bis(phenylsulfonyl)sulfide (manufactured by Across) (compound of the formulae (3) and (4)) was charged at once at −75° C. and the temperature was gradually raised to room temperature over a period of overnight. A saturated aqueous sodium chloride solution was added, then phase separation was conducted, and the organic phase was washed with an aqueous sodium chloride solution. After concentration under reduced pressure, toluene was added to the resulting residue and, after stirring, the whole was allowed to stand. The supernatant was removed and the residue was dried under reduced pressure to obtain crystals (59 mg, yield 25%).

MS m/z: 390 (M$^+$, 100%), 195 (M$^+$/2, 11)

From the MS measurement, it was confirmed that dibenzodithienoacene was obtained. The following shows its structural formula.

[Chem 32]

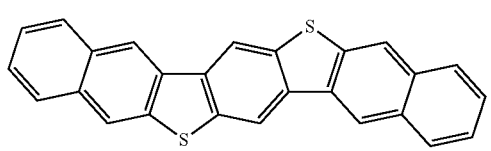

Synthetic Example 4

Synthesis of 2-Bromo-3-iodo-6,7-didodecylanthracene

1) Synthesis of 1,2-Didodecylbenzene 1,2-Didodecylbenzene was synthesized with reference to the method described in "Synthesis", 1993, pp. 387-390 from 1,2-dichlorobenzene and n-dodecylmagnesium bromide as follows.

To a 200 ml Schlenk reaction vessel were added under a nitrogen atmosphere 2.7 ml (24.0 mmol) of 1,2-dichlorobenzene, 66 mg (0.12 mmol) of nickel chloride {bis(diphenylphosphino)propane}, and 18 ml of diethyl ether. The whole was cooled to 0° C. and 65 ml (65 mmol) of a diethyl ether solution of n-dodecylmagnesium bromide (manufactured by Sigma-Aldrich, 1.0M) was added dropwise. After 11 hours of the reaction at 35° C., the reaction was stopped by adding 3N hydrochloric acid. The mixture was extracted with diethyl ether and the organic phase was washed with water and a saturated aqueous sodium hydrogen carbonate solution. The phase was dried over calcium chloride and the solvent was concentrated under reduced pressure. The residue was dried under vacuum (20 Pa) at 170° C. to obtain a liquid of 1,2-didodecylbenzene (8.36 g, yield 84%).

2) Synthesis of 4-Bromo-5-iodophthalic anhydride

4-Bromo-5-iodophthalic anhydride was synthesized with reference to the method described in "Journal of Organic Chemistry" (USA), 1951, vol. 16, pp. 1577-1581 from 4-bromophthalic anhydride as follows.

To a 100 ml three-necked flask were added 6.42 g (28.3 mmol) of 4-bromophthalic anhydride (manufactured by Tokyo Chemical Industry Co. Ltd.), 25 ml of 10% fuming sulfuric acid, and 3.60 g (14.2=mol) of iodine. The mixture was heated to 110° C. and the reaction was carried out for 4 hours. After cooling at room temperature, the reaction mixture was poured into ice to quench the reaction. After the mixture was treated with a cold 20% aqueous sodium hydroxide solution, hydrochloric acid was added to adjust the pH of the solution to 6 to 7. Insoluble matter was removed by means of a filter paper and hydrochloric acid was added portionwise to adjust the pH to 1 or lower. After the resulting slurry was stirred overnight, the formed precipitate was filtrated and dried. The resulting solid was washed with toluene and the residue was treated with a cold 20% aqueous sodium hydroxide solution and dissolved therein. The pH of the solution was adjusted to 3.5 with acetic acid and the formed precipitate was removed by filtration. After the precipitate was treated with hydrochloric acid, the precipitate was further treated with toluene and acetic anhydride to obtain 1.10 g of 4-bromo-5-iodophthalic anhydride (yield 11%).

3) Synthesis of 2-Bromo-3-iodo-6,7-didodecylanthraquinone

2-Bromo-3-iodo-6,7-didodecylanthraquinone was synthesized with reference to the method described in "Berichte" (Germany), 1933, vol. 66B, pp. 1876-1891 as follows.

To a 100 ml three-necked flask were added 1.00 g (2.83=mol) of 4-bromo-5-iodophthalic anhydride synthesized in the above, 1.29 g (3.11 mmol) of 1,2-didodecylbenzene, and 4 ml of tetrachloroethane. Thereto was added 0.82 g (6.15 mmol) of aluminum chloride, followed by 3 hours of stirring at room temperature. Ice was added portionwise to the resulting reaction mixture to quench the reaction, followed by extraction with toluene. The extract was concentrated under reduced pressure to obtain 2.5 g of a viscous matter. To the viscous matter was added 8 ml of sulfuric acid, followed by 2 hours of stirring at 80° C. The resulting reaction mixture was cooled to room temperature and ice was added. The mixture was extracted with toluene and the organic phase was dried over sodium sulfate. Then, the phase was filtered and concentrated under reduced pressure to obtain 678 mg of 2-bromo-3-iodo-6,7-didodecylanthraquinone (yield 35%).

4) Synthesis of 2-Bromo-3-iodo-6,7-didodecylanthracene

After 14 ml of THF was added to 678 mg of 2-bromo-3-iodo-6,7-didodecylanthraquinone obtained in the above and the compound was dissolved therein, 2.7 ml (2.7 mmol) of a toluene solution of diisopropylaluminum hydride (manufactured by Kanto Chemical Co., Ltd., 0.99M) was added, followed by 2 hours of stirring at room temperature. After ice cooling, 5 ml of 6N hydrochloric acid was added and then the mixture was heated to 65° C., followed by 4 hours of reaction. Toluene and an aqueous sodium chloride solution were added thereto and phase separation was conducted. Further, after washing with an aqueous sodium chloride solution, the organic phase was concentrated under reduced pressure and dried under vacuum. The obtained residue was again subjected to repeated reduction with diisopropylaluminum hydride and dehydration operation with 6N hydrochloric acid. The crude product was purified by recrystallization from toluene to obtain 469 mg of 2-bromo-3-iodo-6,7-didodecylanthracene as a light yellow solid (yield 72%).

Example 12

Synthesis of 3,2',5',3"-Tetrabromo-6,7,6",7"-(tetradodecyl)-2,1',4',2"-dinaphthoterphenyl (tetrahaloterphenyl derivative)

To a 100 ml Schlenk reaction vessel were added under a nitrogen atmosphere 461 mg (0.640 mmol) of 2-bromo-3-iodo-6,7-didodecylanthracene synthesized in Synthetic Example 4 and 8 ml of THF. The solution was cooled to −40° C. and 1.0 ml (0.65 mmol) of a THF solution of isopropylmagnesium bromide (manufactured by Kanto Chemical Co., Ltd., 0.65M) was added dropwise. After 30 minutes of aging, the mixture was cooled to −78° C. and 0.65 ml (0.65 mmol) of a diethyl ether solution of zinc chloride (manufactured by Sigma-Aldrich, 1.0M) was added dropwise. After the temperature was gradually raised to room temperature, the resulting reaction liquid was concentrated under reduced pressure. To the obtained residue were added 145 mg (0.298 mmol) of 1,4-dibromo-2,5-diiodobenzene synthesized in Synthetic Example 1, 27.5 mg (0.0238=mol) of tetrakis(triphenylphosphine)-palladium (manufactured by Tokyo Chemical Industry Co. Ltd.), and 8 ml of THF. After the reaction was carried out at 60° C. for 7 hours, the vessel was cooled with water and the reaction was stopped by adding 3 ml of 3N hydrochloric acid. After toluene was added, phase separation was conducted, and the organic phase was washed with an aqueous sodium chloride solution. The organic phase was concentrated under reduced pressure, the solvent was removed by distillation, and further drying was conducted under vacuum. Toluene was added to the resulting residue and a 70% tert-butyl hydroperoxide solution (manufactured by Wako Pure Chemical Industries, Ltd.) (0.06 ml) was added, followed by 2 hours of stirring at room temperature. The solution was washed with water and the organic phase was concentrated under reduced pressure to effect precipitation. The residue was filtrated through a column chromatography packed with silica gel (solvent; hexane:chloroform=5:2) and the filtrate was concentrated under reduced pressure. The obtained residue was washed with hexane and then dried under vacuum to obtain 254 mg of a yellow solid (yield 60%).

MS m/z: 1419 (M$^+$, 100%), 1339 (M$^+$-Br, 8), 1108 (M$^+$-2C$_{11}$H$_{23}$, 15).

From the MS measurement, it was confirmed that 3,2',5',3"-tetrabromo-6,7,6",7"-(tetradodecyl)-2,1',4',2"-dinaphthoterphenyl was obtained. The following shows its structural formula.

[Chem 33]

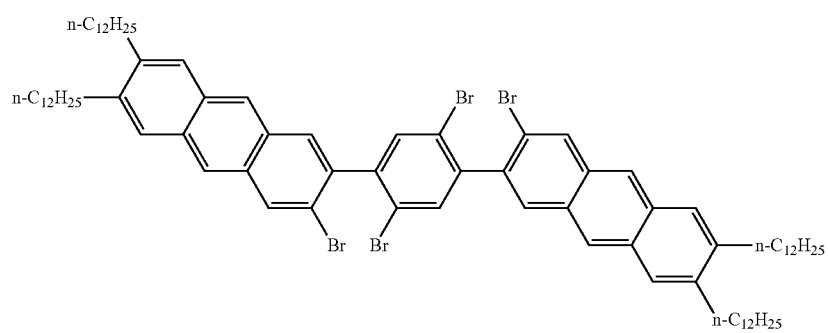

Example 13

Synthesis of Tetradodecyldinaphthodithienoacene (Heteroacene Derivative)

To a 100 ml Schlenk reaction vessel were added under a nitrogen atmosphere 122 mg (0.086 mmol) of 3,2',5',3''-tetrabromo-6,7,6'',7''-(tetradodecyl)-2,1',4',2''-dinaphthoterphenyl synthesized in Example 12 and 6 ml of THF. The suspension solution was cooled to −75° C. and 0.7 ml (0.7 mmol) of a cyclohexane/hexane solution of sec-butyllithium (manufactured by Kanto Chemical Co., Ltd., 1.0M) was added dropwise as a metalation agent to effect tetrametalation. After 20 minutes of stirring, 108 mg (0.344 mmol) of bis(phenylsulfonyl)sulfide (manufactured by Across) (compound of the formulae (3) and (4)) was charged at once at −80° C. and the temperature was gradually raised to room temperature over a period of overnight. Toluene and a saturated aqueous sodium chloride solution were added, then phase separation was conducted, and the organic phase was washed with an aqueous sodium chloride solution, dried over sodium sulfate, and concentrated under reduced pressure. The obtained residue was purified by recrystallization from toluene to obtain 25 mg of a solid (yield 25%).

MS m/z; 1164 ($M^+$, 100%), 582 ($M^+/2$, 14)

From the MS measurement, it was confirmed that tetradodecyldinaphthodithienoacene was obtained. The following shows its structural formula.

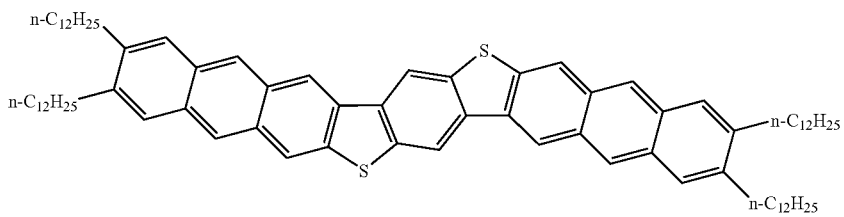

[Chem 34]

Example 14

Synthesis of Tetradodecyldinaphthodithienoacene (Heteroacene Derivative)

A 100 ml Schlenk reaction vessel was cooled to −75° C. under a nitrogen atmosphere, and 6 ml of THF and 1.0 ml (1.0 mmol) of a cyclohexane/hexane solution of sec-butyllithium (manufactured by Kanto Chemical Co., Ltd., 1.0M) as a metalation agent were added. Under 75° C., 132 mg (0.093 mmol) of 3,2',5',3''-tetrabromo-6,7,6'',7''-(tetradodecyl)-2,1', 4',2''-dinaphthoterphenyl synthesized in Example 12 was charged thereto to effect tetrametalation. After 20 minutes of stirring, 117 mg (0.372 mmol) of bis(phenylsulfonyl)sulfide (manufactured by Across) (compound of the formulae (3) and (4)) was charged at once at −80° C. and the reaction temperature was gradually raised to room temperature over a period of overnight. Toluene and a saturated aqueous sodium chloride solution were added, then phase separation was conducted, and the organic phase was washed with an aqueous sodium chloride solution, dried over sodium sulfate, and concentrated under reduced pressure. The obtained residue was purified by recrystallization from toluene to obtain 40 mg of tetradodecyldinaphthodithienoacene (yield 37%).

Example 15

Synthesis of Oxidation-Resistant Organic Semiconductor Material and Evaluation of Oxidation Resistance Under a nitrogen atmosphere, 5.4 g of chlorobenzene was added to a 100 ml Schlenk vessel and dissolved oxygen was removed by repeating three times a cycle composed of freezing (liquid nitrogen)-pressure reduction-replacement with nitrogen-melting. Thereto was added 5.1 mg of a solid of tetrathienoacene obtained in Example 2. The whole was heated and dissolved at 50° C. to synthesize an oxidation-resistant organic semiconductor material containing tetrathienoacene (a bright yellow solution). Then, an upper stopcock of the Schlenk vessel was opened and air was introduced by bringing the vessel into contact with open air for 1 minute (evaluation of oxidation resistance), followed by stirring at 50° C. However, no change in color was observed. Thus, since no change in color was observed, the material was found to be excellent in oxidation resistance.

Example 16

Preparation of Organic Thin Film

Under a nitrogen atmosphere, 2.5 mg of tetrathienoacene obtained in Example 2 was mixed with 25 g of chlorobenzene and the whole was stirred at 70° C. for 1 hour to prepare a bright yellow solution of tetrathienoacene (synthesis of oxidation-resistant organic semiconductor material containing tetrathienoacene).

Under a nitrogen atmosphere, a concavely curved glass substrate is heated at 70° C. and the above solution was applied on the substrate using a dropper and dried under normal pressure to prepare an organic thin film having a film thickness of 280 nm.

Example 17

Synthesis of Oxidation-Resistant Organic Semiconductor Material and Evaluation of Oxidation Resistance Under a nitrogen atmosphere, 5.4 g of chlorobenzene was added to a 100 ml Schlenk vessel and dissolved oxygen was removed by repeating three times a cycle composed of freezing (liquid nitrogen)-pressure reduction-replacement with nitrogen-melting. Thereto was added 7.2 mg of a solid of tetradodecyldinaphthodithienoacene obtained in Example 14. The whole was heated and dissolved at 70° C. to synthesize an oxidation-resistant organic semiconductor material containing tetradodecyldinaphthodithienoacene (a yellowish orange solution). Then, an upper stopcock of the Schlenk vessel was opened and air was introduced by bringing the vessel into contact with open air for 1 minute (evaluation of oxidation resistance), followed by stirring at 70° C. However, no change in color was observed. Thus, since no change in color was observed, the material was found to be excellent in oxidation resistance.

Even when the solution was further brought into contact with air at 70° C. for 1 hour under stirring, no change in color was observed and thus the material was found to be excellent in oxidation resistance.

Example 18

Preparation of Organic Thin Film

Under a nitrogen atmosphere, 4.7 mg of tetradodecyldinaphthodithienoacene obtained in Example 14 was mixed with 15 g of chlorobenzene and the whole was stirred at 70° C. for 1 hour to prepare a yellowish orange solution of tetradodecyldinaphthodithienoacene (synthesis of oxidation-resistant organic semiconductor material containing tetradodecyldinaphthodithienoacene).

Under a nitrogen atmosphere, a concavely curved glass substrate is heated at 70° C. and the above solution was applied on the substrate using a dropper and dried under normal pressure to prepare an organic thin film having a film thickness of 220 nm.

Comparative Example 1

Evaluation of Oxidation Resistance

Oxidation resistance was evaluated using pentacene.

Under a nitrogen atmosphere, 2.9 g of o-dichlorobenzene was added to a 20 ml Schlenk vessel and dissolved oxygen was removed by repeating three times a cycle composed of freezing (liquid nitrogen)-pressure reduction-replacement with nitrogen-melting. Thereto was added 2.5 mg of pentacene (manufactured by Tokyo Chemical Industry Co. Ltd.). When the whole was heated and dissolved at 120° C., a reddish purple solution was formed. Then, an upper stopcock of the Schlenk vessel was opened and air was introduced by bringing the vessel into contact with open air for 1 minute, followed by stirring at 120° C. Based on gas chromatography and gas chromatography-mass spectroscopy (GCMS) analyses, it was found that 6,13-pentacenequinone was formed.

Further, when the solution was brought into contact with air at 120° C. for 1 hour under stirring, the color of the solution changed into yellow. Based on gas chromatography analysis, it was found that the formation of 6,13-pentacenequinone increased.

Thus, since the color of the solution changed and 6,13-pentacenequinone was formed, the compound was found to be poor in oxidation resistance.

While the invention has been described in detail and with reference to specific embodiments thereof, it will be apparent to one skilled in the art that various changes and modifications can be made therein without is departing from the spirit and scope thereof.

The present application is based on Japanese Patent Application No. 2006-231082 filed on Aug. 28, 2006 and the contents are incorporated herein by reference.

INDUSTRIAL APPLICABILITY

According to the present invention, there can be provided a heteroacene derivative having an excellent oxidation resistance and capable of forming an organic semiconductor active phase by a coating process and a use thereof. Furthermore, there can be also provided a tetrahaloterphenyl derivative which is a precursor compound of the heteroacene derivative and a process for producing the same.

The invention claimed is:

1. A heteroacene derivative represented by the following formula (1):

[Chem 1]

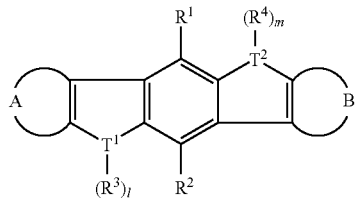

(1)

wherein the substituents $R^1$ to $R^4$ are the same or different and each represents a hydrogen atom, a fluorine atom, a chlorine atom, an aryl group having 4 to 30 carbon atoms, an alkyl group having 3 to 20 carbon atoms, or a halogenated alkyl group having 1 to 20 carbon atoms; $T^1$ and $T^2$ are the same or different and each represents sulfur, selenium, tellurium, phosphorus, boron, or aluminum; l and m each is an integer of 0 or 1; and rings A and B are the same or different and each has a structure represented by the following formulae (A-1):

[Chem 2]

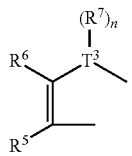

(A-1)

wherein the substituents $R^5$ to $R^7$ are the same or different and each represents a hydrogen atom, a fluorine atom, a chlorine atom, an aryl group having 4 to 30 carbon atoms, an alkyl group having 3 to 20 carbon atoms, or a halogenated alkyl group having 1 to 20 carbon atoms; the substituents $R^5$ and $R^6$ may be together combined to form a substituted or unsubstituted benzene ring, a substituted or unsubstituted pyridine ring, or a substituted or unsubstituted pyrazine ring; the substituent $T^3$ represents sulfur, selenium, tellurium or oxygen and n is an integer of 0.

2. The heteroacene derivative according to claim 1, wherein l and m each is 0 and $T^1$ and $T^2$ are the same or different and each is sulfur, selenium, or tellurium.

3. The heteroacene derivative according to claim 1, wherein l and m each is 1 and $T^1$ and $T^2$ are the same or different and each is phosphorus, boron, or aluminum.

4. An oxidation-resistant organic semiconductor material comprising the heteroacene derivative according to claim 1.

5. An organic thin film, wherein the oxidation-resistant organic semiconductor material according to claim 4 is used.

6. The organic thin film according to claim 5, wherein the organic thin film is formed on a substrate.

* * * * *